United States Patent
Taylor et al.

(10) Patent No.: US 6,585,935 B1
(45) Date of Patent: Jul. 1, 2003

(54) ELECTRO-KINETIC ION EMITTING FOOTWEAR SANITIZER

(75) Inventors: Charles E. Taylor, Sebastopol, CA (US); Shek Fai Lau, Foster City, CA (US)

(73) Assignee: Sharper Image Corporation, San Francisco, CA (US)

( * ) Notice: Subject to any disclaimer, the term of this patent is extended or adjusted under 35 U.S.C. 154(b) by 0 days.

(21) Appl. No.: 09/197,131

(22) Filed: Nov. 20, 1998

(51) Int. Cl.⁷ ................................................ A61L 9/22
(52) U.S. Cl. ..................................... 422/29; 422/186.07
(58) Field of Search ..................... 422/5, 28, 186.05, 422/186.07, 29; 34/253, 389, 380, 390, 442

(56) References Cited

U.S. PATENT DOCUMENTS

| | | | |
|---|---|---|---|
| 2,327,588 A | 8/1943 | Bennett | 315/326 |
| 2,590,447 A | 3/1952 | Nord et al. | 128/393 |
| 2,949,550 A | 8/1960 | Brown | 310/5 |
| 3,793,744 A * | 2/1974 | Saita | 422/300 X |
| 3,981,695 A | 9/1976 | Fuchs | 55/138 |
| 3,984,215 A | 10/1976 | Zucker | 55/2 |
| 4,052,177 A | 10/1977 | Kide | 55/139 |
| 4,102,654 A | 7/1978 | Pellin | 96/16 |
| 4,138,233 A | 2/1979 | Masuda | 55/139 |
| 4,198,765 A * | 4/1980 | Miyamae | 34/104 |
| 4,209,306 A | 6/1980 | Feldman et al. | 55/2 |
| 4,227,894 A | 10/1980 | Proynoff | 96/58 |
| 4,231,766 A | 11/1980 | Spurgin | 55/138 |
| 4,232,355 A | 11/1980 | Finger et al. | 361/235 |
| 4,244,712 A | 1/1981 | Tongret | 55/124 |
| 4,259,452 A | 3/1981 | Yukuta et al. | 521/52 |

(List continued on next page.)

FOREIGN PATENT DOCUMENTS

| | | | |
|---|---|---|---|
| FR | 2690509 | | 10/1993 |
| JP | 10-137007 A | * | 5/1998 |
| JP | 11-104223 A | * | 4/1999 |
| JP | 2000-236914 A | * | 9/2000 |
| WO | WO 01/47803 A1 | | 7/2001 |
| WO | WO 01/48781 A1 | | 7/2001 |

OTHER PUBLICATIONS

U.S. patent application Ser. No. 09/669,253, Taylor et al., filed Sep. 25, 2000.
U.S. patent application Ser. No. 09/669,268, Taylor et al., filed Sep. 25, 2000.
U.S. patent application Ser. No. 09/730,499, Taylor et al., filed Dec. 5, 2000.

(List continued on next page.)

*Primary Examiner*—Elizabeth McKane
(74) *Attorney, Agent, or Firm*—Fliesler Dubb Meyer & Lovejoy LLP

(57) ABSTRACT

A footwear sanitizing device is insertable into footwear to be sanitized. The device includes a self-contained ion generator that subjects the footwear to an outflow of ionized air containing safe amounts of ozone. The ion generator includes a high voltage generator whose output pulses are coupled between first and second electrode arrays disposed in a pair of electrode assemblies. Preferably each first array comprises at least one metal pin spaced coaxially-apart from a metal ring-like structure. Alternatively, the first array may comprise at least one wire electrodes spaced staggeringly apart from a second array comprising hollow "U"-shaped electrodes. Preferably a ratio between effective area of an electrode in the second array compared to effective area of an electrode in the first array exceeds about 15:1 and preferably is about 20:1. An electric field produced by the high voltage between the arrays produces an electrostatic flow of ionized air containing safe amounts of ozone. The outflow of ionized air and ozone is directed toward the footwear being sanitizer.

25 Claims, 13 Drawing Sheets

U.S. PATENT DOCUMENTS

| | | | | |
|---|---|---|---|---|
| 4,266,948 A | | 5/1981 | Teague et al. | 55/126 |
| 4,282,014 A | | 8/1981 | Winkler et al. | 55/105 |
| 4,342,571 A | | 8/1982 | Hayashi | 55/137 |
| 4,386,395 A | | 5/1983 | Francis, Jr. | 363/27 |
| 4,413,225 A | | 11/1983 | Donig et al. | 323/246 |
| 4,445,911 A | | 5/1984 | Lind | 55/2 |
| 4,477,263 A | | 10/1984 | Shaver et al. | 55/6 |
| 4,496,375 A | | 1/1985 | Le Vantine | 55/135 |
| 4,502,002 A | | 2/1985 | Ando | 323/237 |
| 4,536,698 A | | 8/1985 | Shevalenko et al. | 323/237 |
| 4,587,475 A | | 5/1986 | Finney, Jr. et al. | 323/241 |
| 4,600,411 A | | 7/1986 | Santamaria | 55/139 |
| 4,601,733 A | | 7/1986 | Ordines et al. | 55/139 |
| 4,626,261 A | | 12/1986 | Jorgensen | 55/2 |
| 4,632,135 A | | 12/1986 | Lenting et al. | 132/85 |
| 4,643,745 A | | 2/1987 | Sakakibara et al. | 55/137 |
| 4,659,342 A | | 4/1987 | Lind | 55/2 |
| 4,674,003 A | | 6/1987 | Zylka | 361/235 |
| 4,694,376 A | | 9/1987 | Gesslauer | 361/235 |
| 4,713,093 A | | 12/1987 | Hansson | 55/139 |
| 4,713,724 A | | 12/1987 | Voelkel | 361/231 |
| 4,779,182 A | | 10/1988 | Mickal et al. | 363/37 |
| 4,789,801 A | | 12/1988 | Lee | 310/308 |
| 4,798,338 A | | 1/1989 | Bauch et al. | 239/692 |
| 4,808,200 A | | 2/1989 | Dallhammer et al. | 55/105 |
| 4,811,159 A | | 3/1989 | Foster | 361/231 |
| 4,940,470 A | | 7/1990 | Jaisinghani et al. | 55/2 |
| 4,941,068 A | | 7/1990 | Hofmann | 361/231 |
| 5,010,869 A | | 4/1991 | Lee | 123/539 |
| 5,024,685 A | | 6/1991 | Torok et al. | 55/117 |
| 5,072,746 A | | 12/1991 | Kantor | 132/219 |
| 5,141,529 A | | 8/1992 | Oakley et al. | 95/57 |
| 5,215,558 A | | 6/1993 | Moon | 55/129 |
| 5,217,504 A | | 6/1993 | Johansson | 55/2 |
| 5,302,190 A | | 4/1994 | Williams | 95/57 |
| 5,315,838 A | | 5/1994 | Thompson | 62/129 |
| 5,316,741 A | | 5/1994 | Sewell et al. | 422/186.21 |
| 5,378,978 A | | 1/1995 | Gallo et al. | 323/241 |
| 5,386,839 A | | 2/1995 | Chen | 132/152 |
| 5,484,472 A | | 1/1996 | Weinberg | 96/26 |
| 5,535,089 A | | 7/1996 | Ford et al. | 361/231 |
| 5,569,368 A | | 10/1996 | Larsky et al. | 204/600 |
| 5,578,112 A | | 11/1996 | Krause | 96/24 |
| 5,601,636 A | | 2/1997 | Glucksman | 96/63 |
| 5,656,063 A | | 8/1997 | Hsu | 95/58 |
| 5,667,564 A | | 9/1997 | Weinberg | 96/58 |
| 5,702,507 A | | 12/1997 | Wang | 96/55 |
| 5,779,769 A | | 7/1998 | Jiang | 96/55 |
| 5,814,135 A | | 9/1998 | Weinberg | 96/58 |
| 5,879,435 A | | 3/1999 | Satyapal et al. | 96/16 |
| 5,893,977 A | | 4/1999 | Pucci | 210/739 |
| 5,911,957 A | * | 6/1999 | Khatchatrian et al. | 422/28 X |
| 5,972,076 A | | 10/1999 | Nichols et al. | 95/81 |
| 5,975,090 A | | 11/1999 | Taylor et al. | 132/116 |
| 6,019,815 A | | 2/2000 | Satyapal et al. | 95/74 |
| 6,042,637 A | | 3/2000 | Weinberg | 96/58 |
| 6,063,168 A | | 5/2000 | Nichols et al. | 96/80 |
| 6,086,657 A | | 7/2000 | Freije | 95/2 |
| 6,126,722 A | | 10/2000 | Mitchell et al. | 95/57 |
| 6,134,806 A | * | 10/2000 | Dhaemers | 34/404 |
| 6,149,717 A | | 11/2000 | Satyapal et al. | 96/16 |
| 6,149,815 A | | 11/2000 | Sauter | 210/635 |
| 6,152,146 A | | 11/2000 | Taylor et al. | 132/116 |
| 6,163,098 A | | 12/2000 | Taylor et al. | 310/308 |
| 6,176,977 B1 | | 1/2001 | Taylor et al. | 204/176 |
| 6,182,461 B1 | | 2/2001 | Washburn et al. | 62/264 |
| 6,182,671 B1 | | 2/2001 | Taylor et al. | 132/116 |
| 6,193,852 B1 | | 2/2001 | Caracciolo et al. | 204/176 |
| 6,212,883 B1 | | 4/2001 | Kang | 60/275 |
| 6,252,012 B1 | | 6/2001 | Egitto et al. | 525/431 |
| 6,270,733 B1 | | 8/2001 | Rodden | 422/186.07 |
| 6,277,248 B1 | | 8/2001 | Ishioka et al. | 204/176 |
| D449,097 S | | 10/2001 | Smith et al. | D23/364 |
| D449,679 S | | 10/2001 | Smith et al. | D23/365 |
| 6,302,944 B1 | | 10/2001 | Hoenig | 96/16 |
| 6,309,514 B1 | | 10/2001 | Conrad et al. | 204/164 |
| 6,312,507 B1 | | 11/2001 | Taylor et al. | 96/19 |
| 6,315,821 B1 | | 11/2001 | Pillion et al. | 96/416 |
| 6,328,791 B1 | | 12/2001 | Pillion et al. | 96/418 |
| 6,350,417 B1 | | 2/2002 | Lau et al. | 422/186.04 |
| 6,372,097 B1 | | 4/2002 | Chen | 204/176 |
| 6,379,427 B1 | | 4/2002 | Siess | 95/57 |
| 6,391,259 B1 | | 5/2002 | Malkin et al. | 422/28 |

OTHER PUBLICATIONS

U.S. patent application Ser. No. 09/742,814, Taylor et al., filed Dec. 19, 2000.

U.S. patent application Ser. No. 09/774,198, Taylor, filed Jan. 29, 2001.

U.S. patent application Ser. No. 60/306,479, Taylor, filed Jul. 18, 2001.

U.S. patent application Ser. No. 09/924,600, Taylor et al., filed Aug. 8, 2001.

U.S. patent application Ser. No. 09/924,624, Taylor et al., filed Aug. 8, 2001.

U.S. patent application Ser. No. 60/340,288, Taylor, filed Dec. 13, 2001.

U.S. patent application Ser. No. 60/340,462, Taylor, filed Dec. 13, 2001.

U.S. patent application Ser. No. 60/340,702, Taylor et al., filed Dec. 13, 2001.

U.S. patent application Ser. No. 60/341,090, Taylor, filed Dec. 13, 2001.

U.S. patent application Ser. No. 60/341,176, Taylor, filed Dec. 13, 2001.

U.S. patent application Ser. No. 60/341,179, Taylor et al., filed Dec. 13, 2001.

U.S. patent application Ser. No. 60/341,320, Taylor, filed Dec. 13, 2001.

U.S. patent application Ser. No. 60/341,377, Taylor et al., filed Dec. 13, 2001.

U.S. patent application Ser. No. 60/341,433, Taylor, filed Dec. 13, 2001.

U.S. patent application Ser. No. 60/341,518, Taylor, filed Dec. 13, 2001.

U.S. patent application Ser. No. 60/341,592, Taylor, filed Dec. 13, 2001.

U.S. patent application Ser. No. 10/023,197, Taylor et al., filed Dec. 13, 2001.

U.S. patent application Ser. No. 10/023,460, Taylor et al., filed Dec. 13, 2001.

U.S. patent application Ser. No. 10/074,082, Taylor et al., filed Feb. 12, 2002.

U.S. patent application Ser. No. 10/074,096, Taylor et al., filed Feb. 12, 2002.

U.S. patent application Ser. No. 10/074,103, Sinaiko et al., Feb. 12, 2002.

U.S. patent application Ser. No. 10/074,207, Taylor et al., filed Feb. 12, 2002.

U.S. patent application Ser. No. 10/074,208, Taylor, filed Feb. 12, 2002.

U.S. patent application Ser. No. 10/074,209, Taylor et al., filed Feb. 12, 2002.

U.S. patent application Ser. No. 10/074,339, Taylor et al., filed Feb. 12, 2002.

U.S. patent application Ser. No. 10/074,347, Taylor et al., filed Feb. 12, 2002.
U.S. patent application Ser. No. 10/074,549, Sinaiko et al., filed Feb. 12, 2002.
U.S. patent application Ser. No. 10/074,827, McKinney, Jr., et al., filed Feb. 12, 2002.
U.S. patent application Ser. No. 10/156,158, Taylor et al., filed May 28, 2002.
U.S. patent application Ser. No. 10/188,668, Taylor et al., filed Jul. 2, 2002.
U.S. patent application Ser. No. 60/391,070, Reeves, filed Jun. 6, 2002.
LENTEK Silā™ Plug–In Air Purifier/Deodorizer product box copyrighted 1999.

"Zenion Elf Device" drawing, prior art.

Electrical Schematic and promotional material available from Zenion Industries, 7 pages. (possibly published prior to Jan. 1998).

Promotional material available from Zenion Industries for the Plasma–Pure 100/200/300, 2 pages. (possibly published prior to Jan. 1998).

Promotional material available from Zenion Industries for the Plasma–Tron, 2 pages. (possibly published prior to Jan. 1998).

* cited by examiner

ELECTRO-KINETIC ION EMITTING FOOTWEAR SANITIZER

FIELD OF THE INVENTION

This invention relates to devices that sanitize footwear and more particularly to methods and devices for electro-kinetically producing a flow of ionized air containing safe amounts of ozone ($O_3$) into such footwear.

BACKGROUND OF THE INVENTION

Shoes, boots, socks, and other footwear can too readily take on an unpleasant odor from the wearer's feet. Indeed, the moist and warm environment within footwear can promote the undesired and unhealthy growth of bacteria or germs. (As used herein, the term footwear will be understood to include shoes, boots, slippers, socks, and the like.)

It is known in the art to attempt to deodorize footwear passively, for example by allowing shoes or the like to air out when not being worn. It is also known to insert a chemical into an empty shoe or boot, naphtha perhaps, to impart an odor that will perhaps dominate the odor from the user's feet.

However such passive techniques are time consuming and do little or nothing to truly sanitize the footwear. Sanitization can be especially troublesome with children's shoes because children during play often interchange shoes.

One can attempt to actively produce an air flow in an empty shoe with a small fan, to help deodorize the shoe. However the relatively bulky fan or blade mechanism often blocks air attempting to flow out of the footwear. Further, simply flowing air into a shoe does little to remove the cause of the odor in the shoe, bacteria or germs that can exist on the insole or inner lining of the shoe.

Techniques are known to actively produce an air flow using electro-kinetic techniques, by which electrical power is directly converted into a flow of air without mechanically moving components. One such system is described in U.S. Pat. No. 4,789,801 to Lee (1988), depicted herein in simplified form as FIGS. 1A and 1B. Lee's system 10 provides a first array of small area ("minisectional") electrodes 20 is spaced-apart symmetrically from a second array of larger area ("maxisectional") electrodes 30, with a high voltage (e.g., 5 KV) pulse generator 40 coupled between the two arrays. Generator 40 outputs high voltage pulses that ionize the air between the arrays, producing an air flow 50 from the minisectional array toward the maxisectional array results. The high voltage field present between the two arrays can release ozone ($O_3$), which can advantageously safely destroy many types of bacteria if excessive quantities of ozone are not released.

Unfortunately, Lee's tear-shaped maxisectional electrodes are relatively expensive to fabricate, most likely requiring mold-casting or extrusion processes. Further, air flow and ion generation efficiency is not especially high using Lee's configuration. A Lee-type electrode configuration would be difficult to mass produce economically for use in a device intended to sanitize footwear.

There is a need for a footwear sanitizer that can not produce an air flow within an empty shoe or boot, but can also provide true sanitizing action. Preferably such a device should subject the interior of the footwear to a flow of ions containing ozone, to promote sanitation, in addition to deodorizing the footwear.

The present invention provides such a sanitizing device.

SUMMARY OF THE PRESENT INVENTION

The present invention provides a footwear sanitizer device whose housing includes a central portion and two projecting members that are spaced-apart a distance to permit inserting each member into a shoe (or the like). The projecting members are sized to slide into the length of the shoe.

An electrode assembly is located within the distal portion of each projecting member, each assembly comprising a first and second array of electrodes. A battery-operated ionizer unit with DC battery power supply is contained within the housing. The ionizer unit includes a DC:DC inverter that boosts the battery voltage to high voltage, and a generator that receives the high voltage DC and outputs high voltage, pulses or DC, of perhaps 10 KV peak-to-peak. The high voltage output from the high voltage generator is coupled between the first and second array of electrodes in each electrode assembly. Preferably each first and second array is coupled respectively to the positive and negative output ports of the high voltage generator.

Each electrode assembly preferably is formed using first and second arrays of readily manufacturable electrode types. In one embodiment, the first array comprises wire-like electrodes and the second array comprises "U"-shaped electrodes having one or two trailing surfaces. In an even more efficient embodiment, the first array includes at least one pin or cone-like electrode and the second array is an annular washer-like electrode. The electrode assembly may comprise various combinations of the described first and second array electrodes. In the various embodiments, the ratio between effective area of the second array electrodes to the first array electrodes is at least about 20:1.

The high voltage creates an electric field between the first and second electrode arrays to produce an electro-kinetic airflow from the first array toward the second array, the airflow being rich in ions and in ozone ($O_3$). Ambient air enters the device through at least one air intake vent, and ionized air (with ozone) exits the distal region of the projecting members through at least one outlet vent. If desired, a single vent in each projecting member can suffice as both an intake and an outlet vent. Preferably a visual indicator is coupled to the ionizer unit to visually confirm to a user when the unit is ready for ionizing operation, and when ionization is actually occurring.

The projecting members are inserted into footwear and the device is turned on, energizing the ion generator. The interior of the footwear is subjected to an outflow of ionized air containing ozone. The resultant airflow not only electro-kinetically airs out the interior of the footwear, but the ozone-rich ionized air flow sanitizes and deodorizes the interior as well.

Other features and advantages of the invention will appear from the following description in which the preferred embodiments have been set forth in detail, in conjunction with the accompanying drawings.

DETAILED DESCRIPTION OF THE PREFERRED EMBODIMENT

Figure 1A:
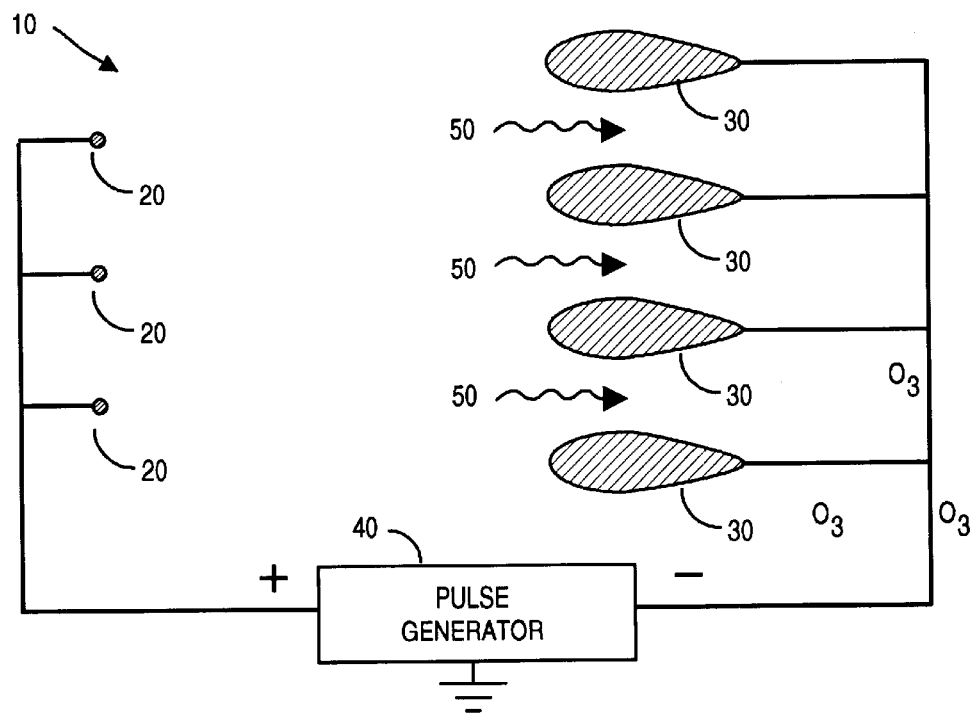
FIGS. 1A and 1B are depictions of Lee-type electrostatic generators, according to the prior art.
Figure 1B:
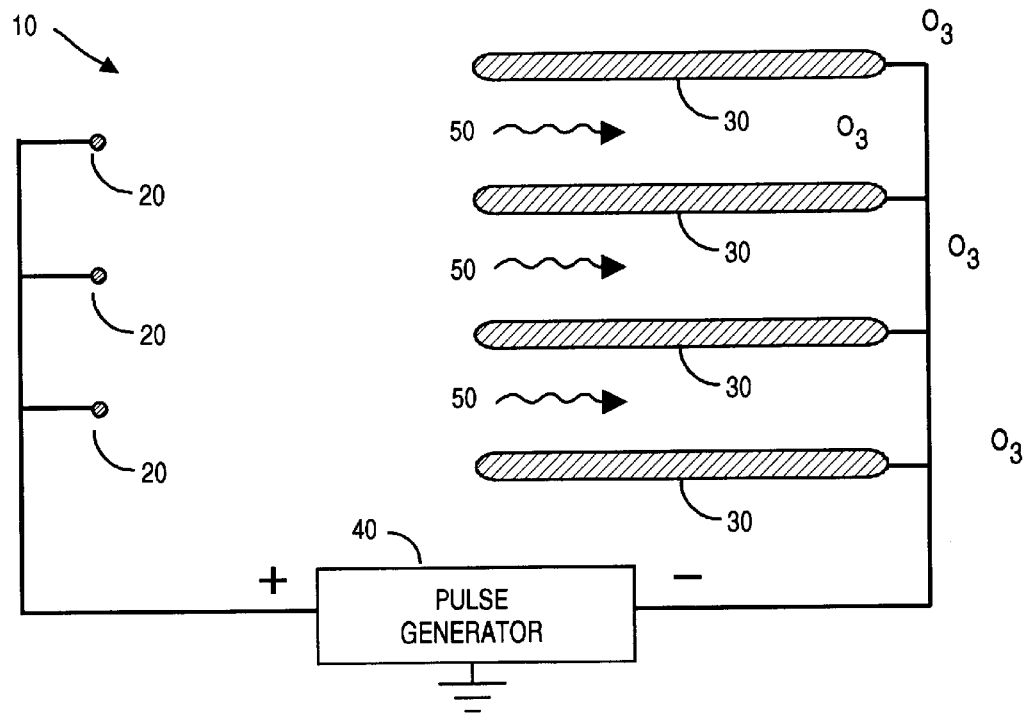
Figure 2:
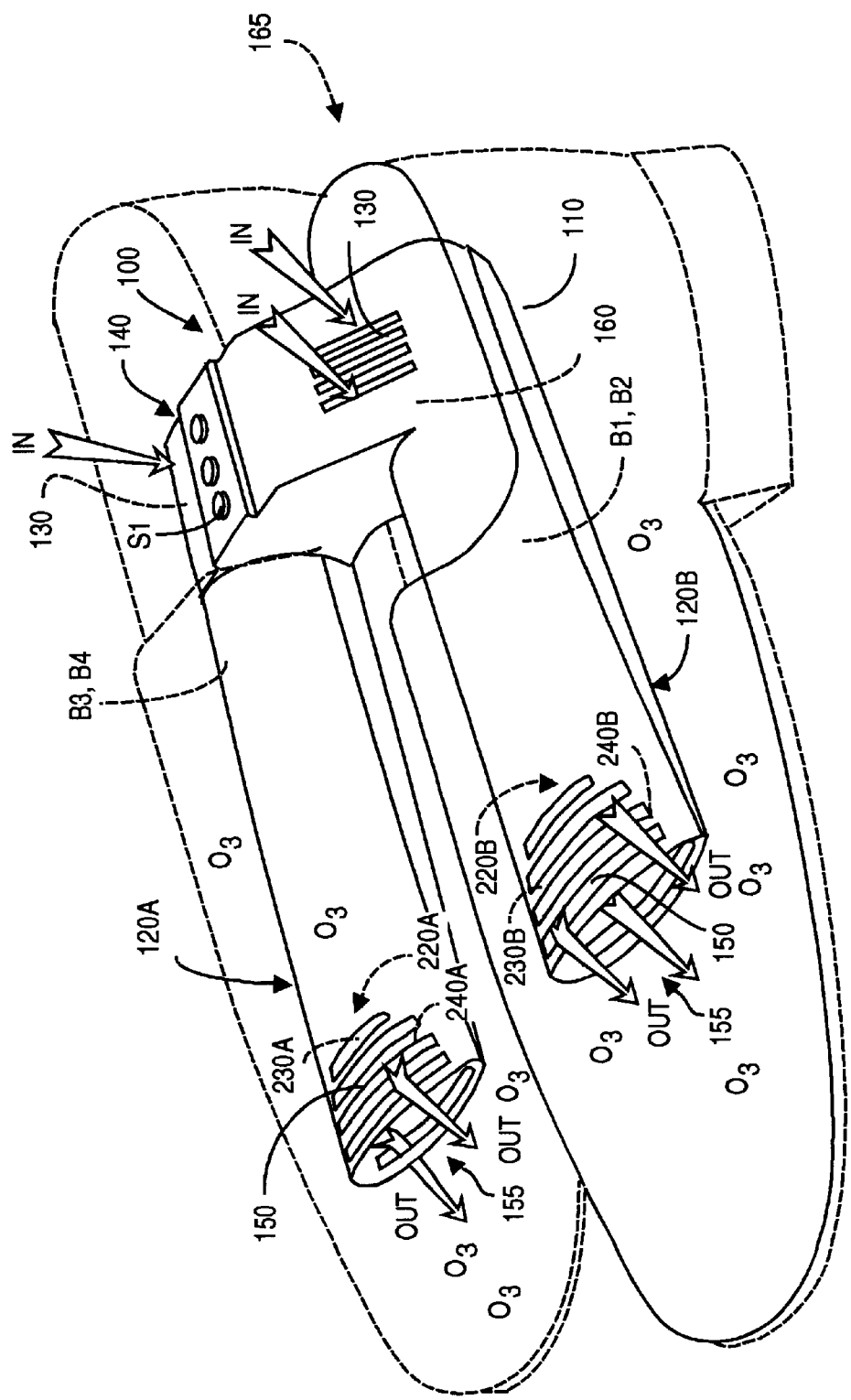
FIG. 2 is perspective view of a preferred embodiment of an ionizing sanitizing device for footwear, according to the present invention.

FIG. 2 depicts an ionizing footwear sanitizer device 100 according to the present invention as having a common housing or body portion 110 with spaced-apart first and second members 120A and 120B projecting therefrom. Body portion 100 preferably includes one or more air intake vents 130, and the projecting members preferably include one or more outlet vents 150. In addition, the distal ends of members 120A and 120B preferably are open, to provide additional outlet venting and to provide user-access for cleaning electrodes in electrode assemblies 220 retained within (as will be described).

The material comprising the external housing for unit 100 is preferably inexpensive, lightweight, and easy to fabricate, ABS plastic for example. Device 100 preferably is sized such that projecting members 120A and 120B can fit within spaced-apart footwear 165, for example shoes, boots, slippers. Thus the total overall length of device 100 may be perhaps 7" (18 cm) and the spaced-apart distance between members 120A and 120B will be a few inches (e.g., 7 cm or so). It will also be appreciated that footwear 165 could indeed be empty sox, or indeed device 100 may be handheld and used to deodorize a user's bare feet or sock-encased feet.

Internal to device 100 is an ion generating unit 160, which comprises various electronic components (described with respect to FIG. 3), as well as first and second electrode assemblies 220A and 220B, disposed respectively near the distal ends 155 of projecting members 120A and 120B. Ion generating unit 160 receives DC operating power, preferably from four batteries B1, B2, B3, B4. In a preferred embodiment, four D-size cells are series-coupled to provide 6 VDC, to ion generating unit 160 via an on/off switch S1. Switch S1 is one of several user-accessible controls 140 mounted on device 100. As such, ion generating unit 160 is self-contained in that other than ambient air, nothing is required external to the body device 100 for operation of the present invention. Of course if desired, a DC power supply could be disposed external to the housing of device 100, and power brought into device 100 via a power cable.

It is understood that the shape or configuration shown in FIG. 2 is only exemplary, and other dimensions and configurations may be used. More or fewer vents 130, 150 may be provided, and the location and/or shapes of these vents can differ from what is depicted in FIG. 2. The role of vents 130 and 150 is to ensure that an adequate flow of ambient air may be drawn into (denoted "IN") or made available to unit 130, and that an adequate flow of ionized air that includes safe amounts of $O_3$ flows out (denoted "OUT") from unit 130 towards the footwear to be sanitized.

Figure 3:
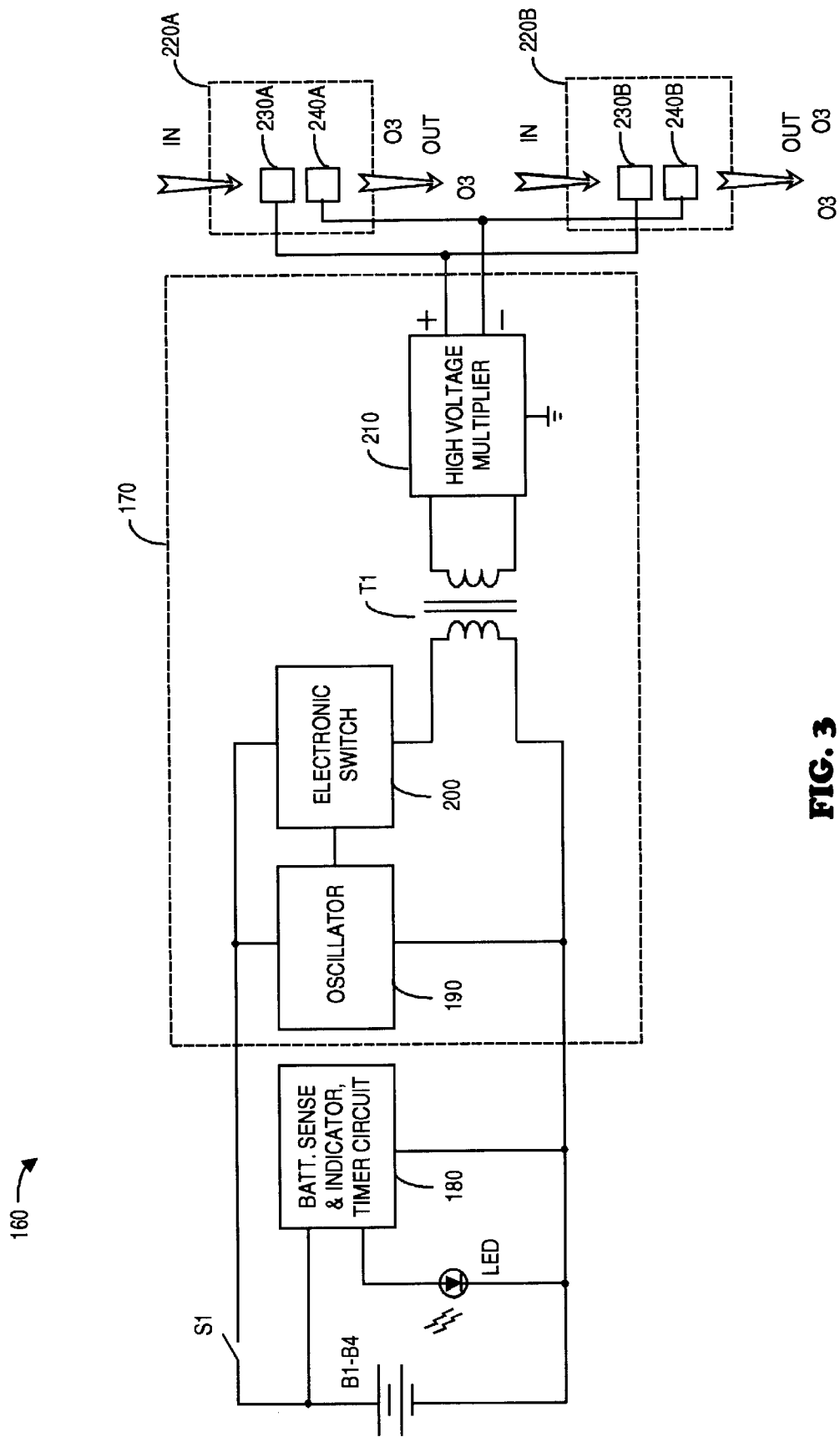
FIG. 3 is an electrical block diagram of the present invention.

As best seen in FIG. 3, ion generating unit 160 includes a high voltage generator unit 170, preferably electronic circuitry 180 to sense and visually indicate battery potential and a circuit permitting timed energization of the ion generating unit. Unit 160 also includes a pair of electrode assemblies 220A and 220B, that each comprise first and second electrode arrays 230A–240A, and 230B–240B respectively. Electrode assemblies 220A and 220B are preferably identical but need not be. Array 220A is disposed in member 120A, and array 220B is disposed in member 120B. As these arrays are identical, they may interchangeably be referred to as array or arrays 220. Similarly first electrode assembly 230A in assembly 220A is preferably identical to first electrode assembly 230B in assembly 220B, and these first electrode assemblies may be referred to interchangeably as 220. Similarly, interchangeable second electrode assemblies 240A and 240B (respectively in assemblies 220A and 220B) may be referred to interchangeably as 220.

As will be described, the application of high voltage between first array electrodes 230 and second array electrodes 240 creates an electro-kinetic airflow (the "OUT" flow) as well as ozone.

Circuit 180 senses potential on the batteries and indicates whether battery potential is sufficient to generate ions, and when ion generation is occurring. In the preferred embodiment, a visual indicator is used, preferably a two-color light emitting diode ("LED"). Of course other indicator devices may be used, including for example, blinking indicator(s), and/or audible indicator(s). Circuit 180 preferably further includes timing components that will turn-off generation of ions and ozone after a predetermined time, for example five minutes. This permits the present invention to be inserted into footwear (e.g., a pair of shoes 165 as indicated in phantom in FIG. 2), and energized with switch S1, for automatic operation for a user-determined or predetermined time period. During that period, an "OUT" airflow is electro-kinetically created, which airflow carries ozone that can kill or at least diminish odors, germs, and/or bacteria in the footwear.

As shown in FIG. 3, high voltage pulse generator unit 170 preferably comprises a low voltage oscillator circuit 190 of perhaps 20 KHz frequency, that outputs low voltage pulses to an electronic switch 200, e.g., a thyristor or the like. Switch 200 switchably couples the low voltage pulses to the input winding of a step-up transformer T1. The secondary winding of T1 is coupled to a high voltage multiplier circuit 210 that outputs high voltage pulses. Preferably the circuitry and components comprising high voltage pulse generator 170 and circuitry 180 are fabricated on a printed circuit board that is mounted within housing 110 of unit 100.

Output from high voltage generator 170 preferably are pulses with at least 10 KV peak-to-peak amplitude, with an effective DC offset of perhaps half the peak-to-peak voltage.

The pulse train has a preferably above-audio frequency of perhaps 20 KHz, and has a duty cycle of perhaps 10%, which will promote battery lifetime. Mechanical vibrations can occur within unit 100, and an above-audio frequency will prevent any such vibrations from being heard by a user. If desired, different peak-peak amplitudes, DC offsets, pulse train waveshapes, duty cycle, and/or repetition frequencies may instead be used. Indeed, a 100% pulse train (e.g., an essentially DC high voltage) may be used, albeit with shorter battery lifetime.

The output from high voltage pulse generator unit 170 is coupled to electrode assemblies 220A and 220B, each of which comprises first and second electrode arrays. Thus, first electrode assembly 220A comprises first electrode array 230A and second electrode array 240A, while second electrode assembly 220B comprises first electrode array 230B and second electrode array 240B. For ease of reference, nomenclature 230 will be understood to refer to a first electrode array 230A and/or 230B, and nomenclature 240 will be understood to refer to a second electrode array 240A and/or 240B.

Unit 170 functions as a DC:DC high voltage generator, and could be implemented using other circuitry and/or techniques to output high voltage pulses that are input to electrode assemblies 220A and 220B.

In the embodiment of FIG. 3, the positive output terminal of unit 170 is coupled to the first electrode arrays 230, and the negative output terminal is coupled to the second electrode arrays 240. This coupling polarity has been found to work well. An electrostatic flow of air is created ("OUT"), going from the first electrode array towards the second electrode array. Accordingly the electrode assemblies 220 are mounted in the distal end portions 155 of members 120 such that the second electrode arrays 240 are downstream (e.g., closer to the very distal end) from first electrode arrays 230.

When voltage or pulses from high voltage pulse generator 170 are coupled across first and second electrode arrays 230 and 240, it is believed that a plasma-like field is created surrounding electrodes 232 in first array 230. This electric field ionizes the air between the first and second electrode arrays and establishes an "OUT" airflow that moves towards the second array. It is understood that at least some of the IN flow enters device 100 via vent(s) 130, and that the OUT flow exits device 100 via vent(s) 150.

It is believed that ozone and ions are generated simultaneously by the first array electrode(s) 232, essentially as a function of the potential from generator 170 coupled to the first array. Ozone generation may be increased or decreased by increasing or decreasing the potential at the first array. Coupling an opposite polarity potential to the second array electrode(s) 242 essentially accelerates the motion of ions generated at the first array, producing the air flow denoted as "OUT" in the figures. As the ions move toward the second array, it is believed that they push or move air molecules toward the second array. The relative velocity of this motion may be increased by decreasing the potential at the second array relative to the potential at the first array.

For example, if +10 KV were applied to the first array electrode(s), and no potential were applied to the second array electrode(s), a cloud of ions (whose net charge is positive) would form adjacent the first electrode array. Further, the relatively high 10 KV potential would generate substantial ozone. By coupling a relatively negative potential to the second array electrode(s), the velocity of the air mass moved by the net emitted ions increases, as momentum of the moving ions is conserved.

On the other hand, if it were desired to maintain the same effective outflow (OUT) velocity but to generate less ozone, the exemplary 10 KV potential could be divided between the electrode arrays. For example, generator 170 could provide +6 KV (or some other fraction) to the first array electrode(s) and −4 KV (or some other fraction) to the second array electrode(s). In this example, it is understood that the +6 KV and the −4 KV are measured relative to ground. Understandable it is desired that the present invention operate to output safe amounts of ozone.

As noted, outflow (OUT) preferably includes safe amounts of $O_3$ that can destroy or at least substantially alter bacteria, germs, and other living (or quasi-living) matter subjected to the outflow. Thus, when switch S1 is closed and B1 has sufficient operating potential, pulses from high voltage pulse generator unit 170 create an outflow (OUT) of ionized air and $O_3$. When S1 is closed, LED will first visually signal whether sufficient Bi potential is present, and if present, then signal when ionization is occurring. If LED fails to indicate sufficient operating voltage, the user will know to replace B1 or, if rechargeable cells are used, to recharge B1. For example, if visual indicator is a two-color device, the LED could signal red when B1 potential exceeds a minimum threshold, e.g., 5.5 VDC. Further, LED could then signal green when S1 is depressed and unit 160 is actually outputting ionized air. If the battery potential is too low, the LED will not light, which advises the user to replace or re-charge battery source B1.

Preferably operating parameters of the present invention are set during manufacture and are not user-adjustable. For example, increasing the peak-to-peak output voltage and/or duty cycle in the high voltage pulses generated by unit 170 can increase air flowrate, ion content, and ozone content. In the preferred embodiment, output flowrate is about 90 feet/minute, ion content is about 2,000,000/cc and ozone content is about 50 ppb (over ambient) to perhaps 2,000 ppb (over ambient). Decreasing the R2/R1 ratio below about 20:1 will decrease flow rate, as will decreasing the peak-to-peak voltage and/or duty cycle of the high voltage pulses coupled between the first and second electrode arrays.

In practice, a user can insert device 100 into footwear 165 as shown in FIG. 2. With S1 energized, ionization unit 160 emits ionized air and preferably some ozone ($O_3$) via outlet vents 150. The interior of the footwear advantageously is subjected to this outflow ("OUT") of air and ozone. Beneficially, the footwear interior is deodorized and the growth of germs, bacteria and the like can be retarded or even eliminated. After a predetermined time period, device 100 can turn itself off. If desired, device 100 could be used to subject a user's bare feet to the outflow ("OUT") of ozone-containing ionized air, to deodorize and sanitize the feet.

Having described various aspects of the invention in general, preferred embodiments of electrode assemblies 220 will now be described. In the various embodiments, each electrode assembly 220 will comprise a first array 230 of at least one electrode 232, and will further comprise a second array 240 of preferably at least one electrode 242. Understandably material(s) for electrodes 232 and 242 should conduct electricity, be resilient to corrosive effects from the application of high voltage, yet be strong enough to be cleaned. Again, it is understood that the preferred embodiment of device 100 will include two electrode assemblies 220, each of which comprises first and second arrays 230, 240, in which each first array includes at least one electrode 232 and in which each second array includes at least one electrode 242.

In the various electrode assemblies to be described herein, electrode(s) 232 in the first electrode array 230 are preferably fabricated from tungsten. Tungsten is sufficiently robust to withstand cleaning, has a high melting point to retard breakdown due to ionization, and has a rough exterior surface that seems to promote efficient ionization. On the other hand, electrodes 242 preferably will have a highly polished exterior surface to minimize unwanted point-to-point radiation. As such, electrodes 242 preferably are fabricated from stainless steel, brass, among other materials. The polished surface of electrodes 232 also promotes ease of electrode cleaning. User access for electrode cleaning is preferably gained through the open distal portions 155 of members 120.

In contrast to the prior art electrodes disclosed by Lee, electrodes 232 and 242 according to the present invention are light weight, easy to fabricate, and lend themselves to mass production. Further, electrodes 232 and 242 described herein promote more efficient generation of ionized air, and production of safe amounts of ozone, $O_3$.

In the present invention, a high voltage pulse generator 170 is coupled between the first electrode array 230 and the second electrode array 240. The high voltage pulses produce a flow of ionized air that travels in the direction from the first array towards the second array (indicated herein by hollow arrows denoted "OUT"). As such, electrode(s) 232 may be referred to as an emitting electrode, and electrodes 242 may be referred to as collector electrodes. This outflow advantageously contains safe amounts of $O_3$, and exits the present invention from vent(s) 150, as shown in FIG. 2. Although a generator of high voltage pulses is preferred and will promote battery life, in practice high voltage DC (e.g., pulses having 100% duty cycle) may instead be used.

According to the present invention, it is preferred that the positive output terminal or port of the high voltage pulse generator be coupled to electrodes 232, and that the negative output terminal or port be coupled to electrodes 242. It is believed that the net polarity of the emitted ions is positive, e.g., more positive ions than negative ions are emitted. In any event, the preferred electrode assembly electrical coupling minimizes audible hum from electrodes 232 contrasted with reverse polarity (e.g., interchanging the positive and negative output port connections). In some embodiments, however, one port (preferably the negative port) of high voltage pulse generator may in fact be the ambient air. Thus, electrodes in the second array need not be connected to the high voltage pulse generator using wire. Nonetheless, there will be an "effective connection" between the second array electrodes and one output port of the high voltage pulse generator, in this instance, via ambient air.

Figure 4A:
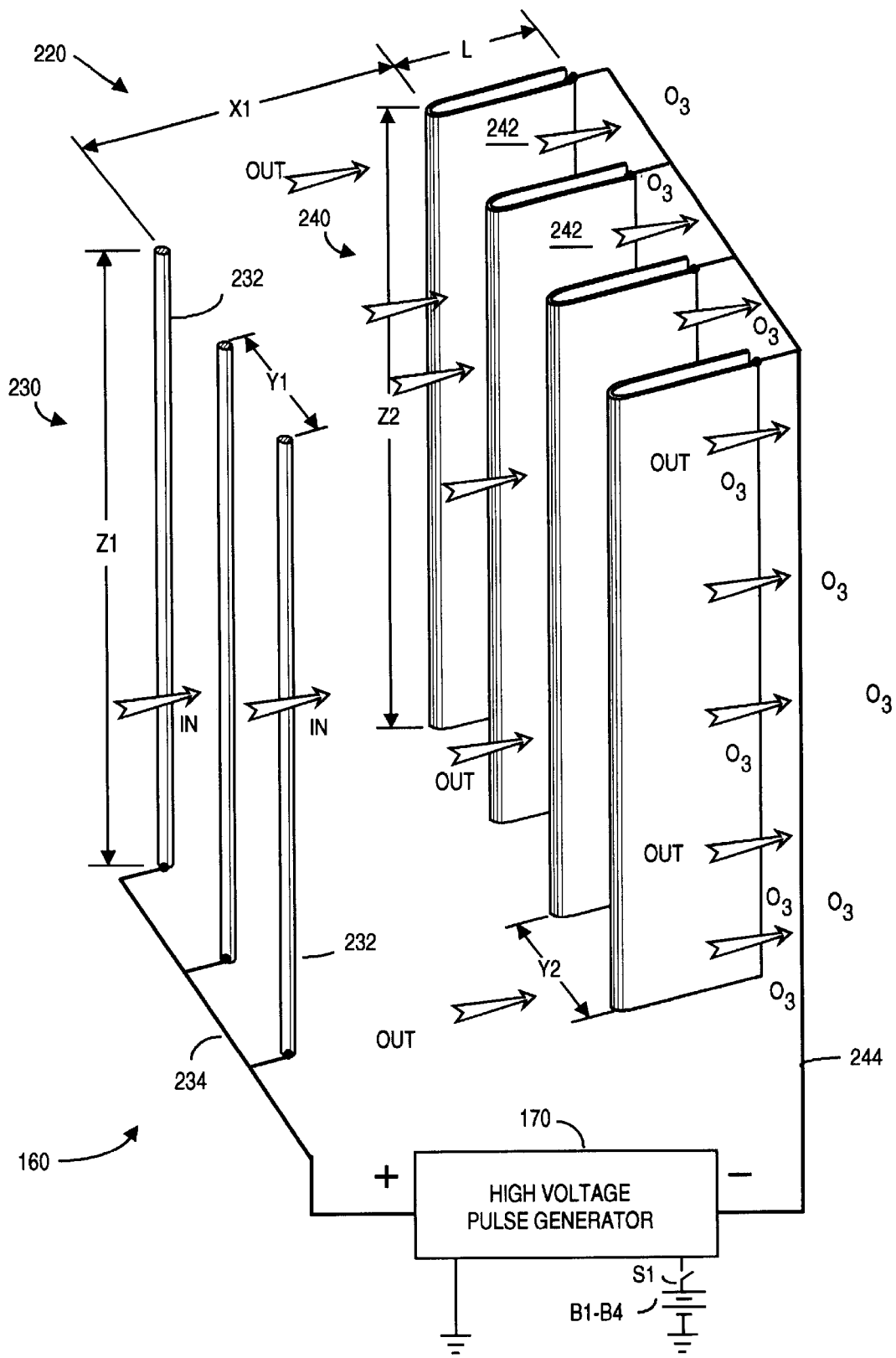
FIG. 4A is a perspective block diagram showing a first embodiment for an electrode assembly, according to the present invention.
Figure 4B:
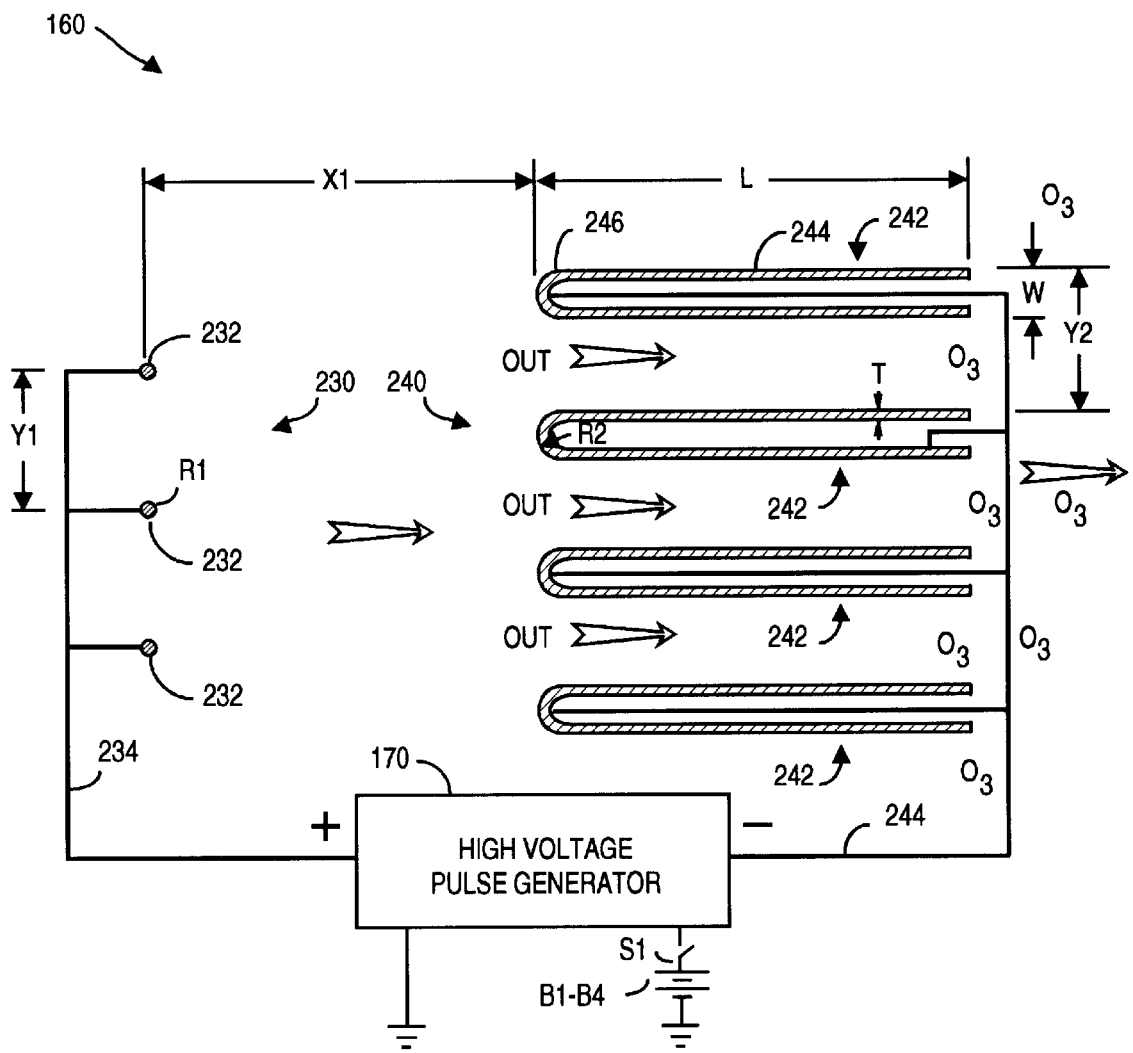
FIG. 4B is a plan block diagram of the embodiment of FIG. 4A.

Turning now to the embodiments of FIGS. 4A and 4B, an exemplary electrode assembly 220 comprises a first array 230 of wire electrodes 232, and a second array 240 of generally "U"-shaped electrodes 242. In preferred embodiments, the number N1 of electrodes comprising the first array will differ by one relative to the number N2 of electrodes comprising the second array. In many of the embodiments shown, N2>N1. However, if desired, in FIG. 4A, addition first electrodes 232 could be added at the out ends of array 230 such that N1>N2, e.g., five electrodes 232 compared to four electrodes 242. Again it is to be understood that generator 170 is coupled to a pair of electrode assemblies 220, each of which contains first and second arrays of at least one electrode each. For ease of illustration, only one electrode assembly is shown in the FIGS. 4A–4I.

Electrodes 232 are preferably lengths of tungsten wire, whereas electrodes 242 are formed from sheet metal, preferably stainless steel, although brass or other sheet metal could be used. The sheet metal is readily formed to define side regions 244 and bulbous nose region 246 for hollow elongated "U" shaped electrodes 242. While FIG. 4A depicts four electrodes 242 in second array 240 and three electrodes 232 in first array 230, as noted, other numbers of electrodes in each array could be used, preferably retaining a symmetrically staggered configuration as shown.

As best seen in FIG. 4B, the spaced-apart configuration between the arrays is staggered such that each first array electrode 232 is substantially equidistant from two second array electrodes 242. This symmetrical staggering has been found to be an especially efficient electrode placement. Preferably the staggering geometry is symmetrical in that adjacent electrodes 232 or adjacent electrodes 242 are spaced-apart a constant distance, Y1 and Y2 respectively. However, a non-symmetrical configuration could also be used, although ion emission and air flow would likely be diminished. Also, it is understood that the number of electrodes 232 and 242 may differ from what is shown.

In FIG. 4A, typically dimensions are as follows: diameter of electrodes 232 is about 0.08 mm, distances Y1 and Y2 are each about 16 mm, distance X1 is about 16 mm, distance L is about 20 mm, and electrode heights Z1 and Z2 are each about 100 mm. The width W of electrodes 242 is preferably about 4 mm, and the thickness of the material from which electrodes 242 are formed is about 0.5 mm. Of course other dimensions and shapes could be used. It is preferred that electrodes 232 be small in diameter to help establish a desired high voltage field. On the other hand, it is desired that electrodes 232 (as well as electrodes 242) be sufficiently robust to withstand occasional cleaning.

Electrodes 232 in first array 230 are coupled by a conductor 234 to a first (preferably positive) output port of high voltage pulse generator 170, and electrodes 242 in second array 240 are coupled by a conductor 244 to a second (preferably negative) output port of generator 170. It is relatively unimportant where on the various electrodes electrical connection is made to conductors 234 or 244. Thus, by way of example FIG. 4B depicts conductor 244 making connection with some electrodes 242 internal to bulbous end 246, while other electrodes 242 make electrical connection to conductor 244 elsewhere on the electrode. Electrical connection to the various electrodes 242 could also be made on the electrode external surface providing no substantial impairment of the outflow airstream results.

The ratio of the effective electric field emanating area of electrode 232 to the nearest effective area of electrodes 242 is at least about 15:1, and preferably is at least 20:1. Beyond a ratio of say 35:1, little or no performance improvement results. Thus, in the embodiment of FIG. 4A and FIG. 4B, the ratio R2/R1≈2 mm/ 0.08 mm≈25:1.

In this and the other embodiments to be described herein, ionization appears to occur at the smaller electrode(s) 232 in the first electrode array 230, with ozone production occurring as a function of high voltage arcing. For example, increasing the peak-to-peak voltage amplitude and/or duty cycle of the pulses from the high voltage pulse generator 170 can increase ozone content in the output flow of ionized air.

Figure 4C:
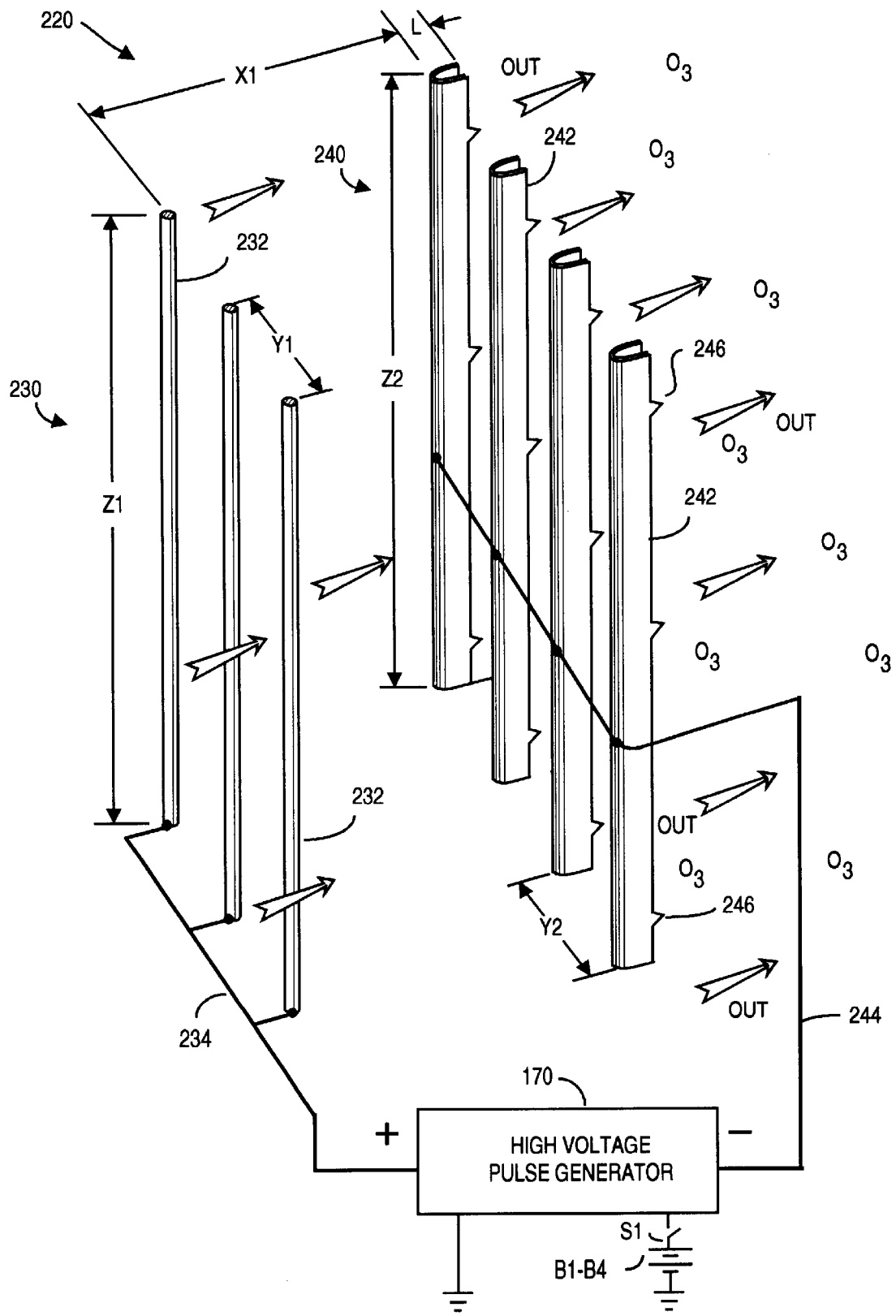
FIG. 4C is a perspective block diagram showing a second embodiment for an electrode assembly, according to the present invention.
Figure 4D:
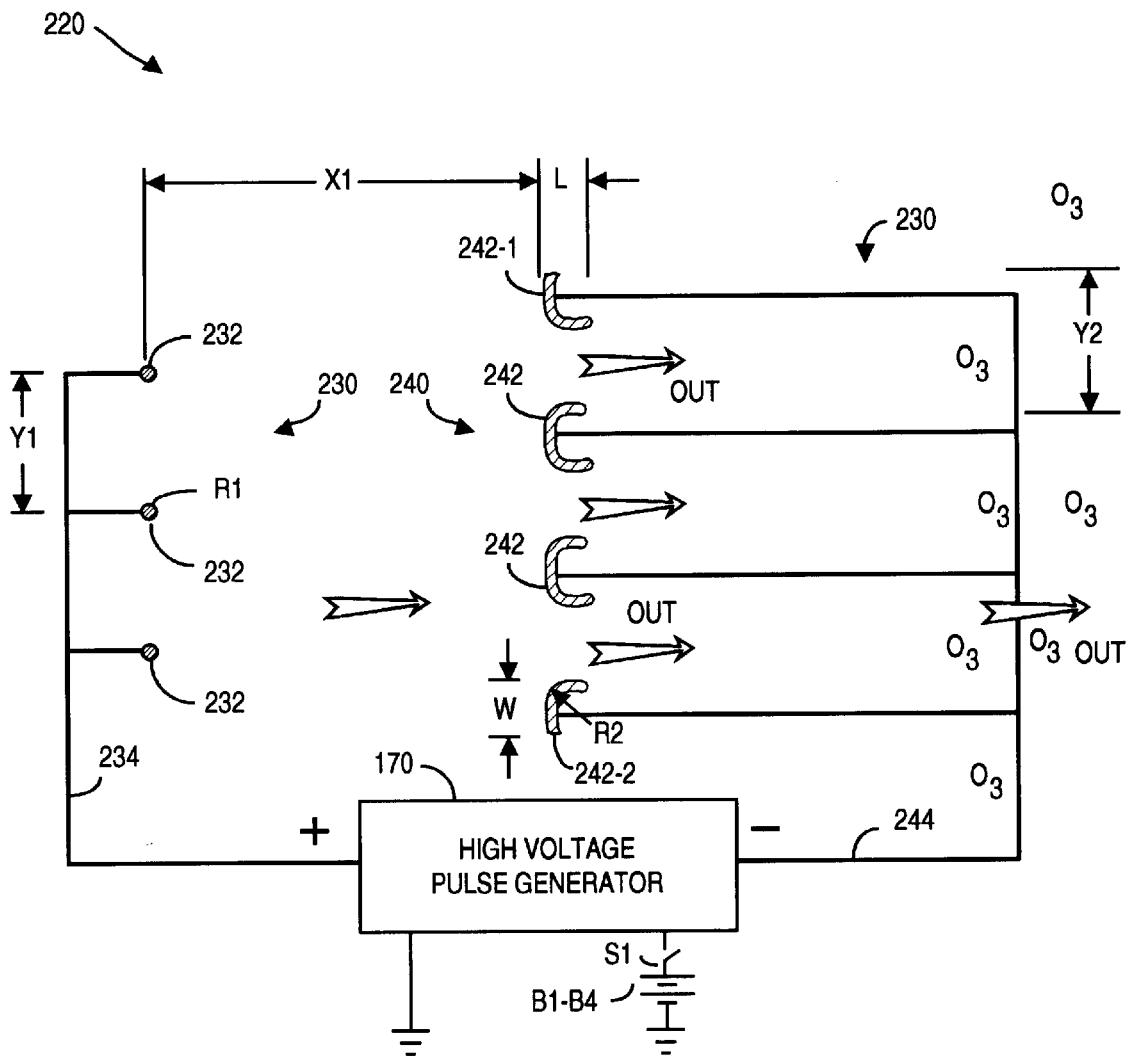
FIG. 4D is a plan block diagram of a modified version of the embodiment of FIG. 4C.

In the embodiment of FIGS. 4A and 4C, each "U"-shaped electrode 242 has two trailing edges 244 that promote efficient kinetic transport of the outflow of ionized air and $O_3$. By contrast, the embodiments of FIGS. 4C and 4D depict somewhat truncated versions of electrodes 242. Whereas dimension L in the embodiment of FIGS. 4A and 4B was about 20 mm, in FIGS. 4C and 4D, L has been shortened to about 8 mm. Other dimensions in FIG. 4C preferably are similar to those stated for FIGS. 4A and 4B. In FIGS. 4C and 4D, the inclusion of point-like regions 246 on the trailing edge of electrodes 242 seems to promote more efficient generation of ionized air flow. It will be appreciated that the configuration of second electrode array 240 in FIG. 4C can be more robust than the configuration of FIGS. 4A and 4B, by virtue of the shorter trailing edge geometry. As noted earlier, a symmetrical staggered geometry for the first and second electrode arrays is preferred for the configuration of FIG. 4C.

In the embodiment of FIG. 4D, the outermost second electrodes, denoted 242-1 and 242-2, have substantially no outermost trailing edges. Dimension L in FIG. 4D is preferably about 3 mm, and other dimensions may be as stated for the configuration of FIGS. 4A and 4B. Again, the R2/R1 ratio for the embodiment of FIG. 4D preferably exceeds about 20:1.

Figure 4E:
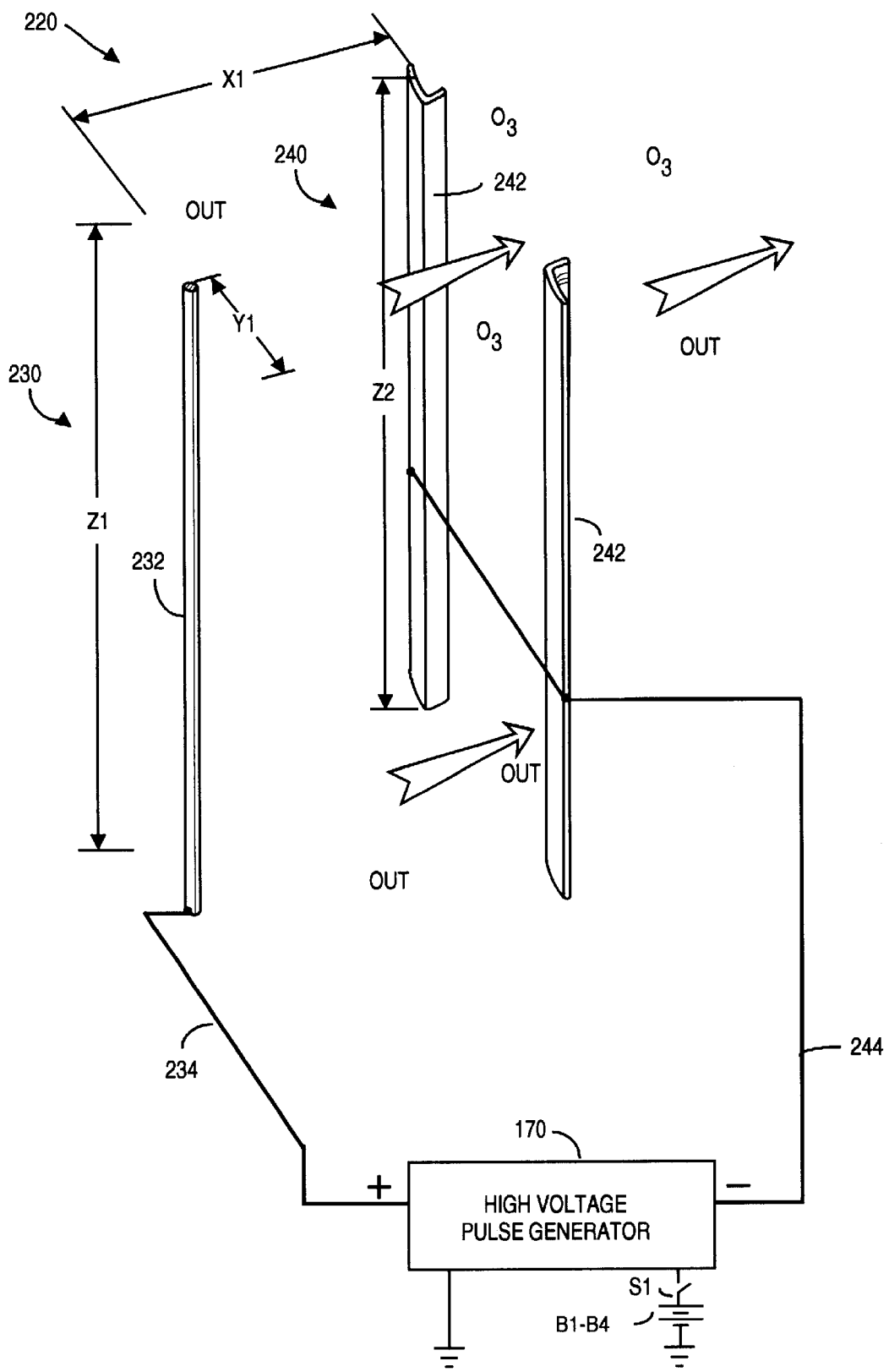
FIG. 4E is a perspective block diagram showing a third embodiment for an electrode assembly, according to the present invention.
Figure 4F:
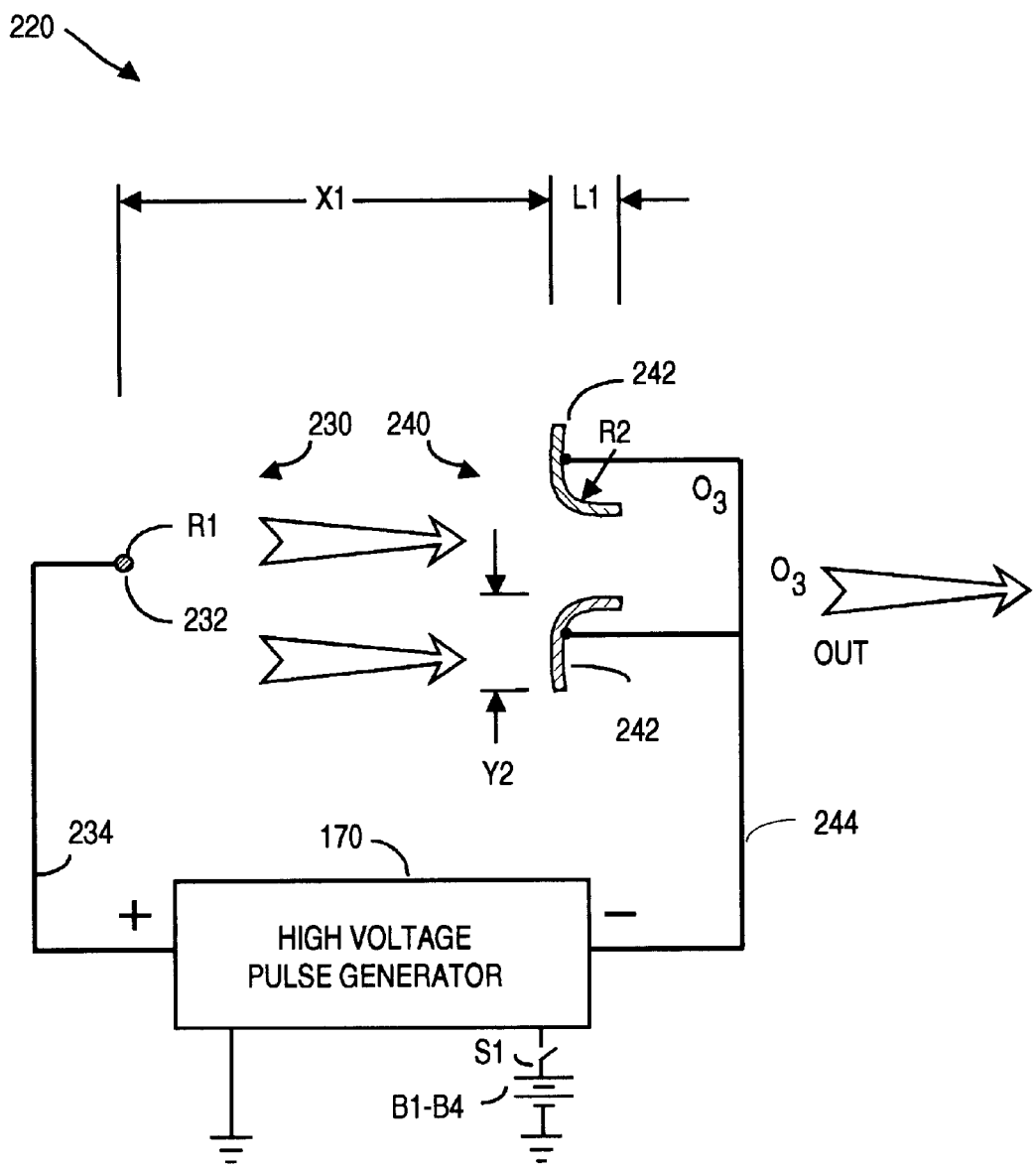
FIG. 4F is a plan block diagram of the embodiment of FIG. 4E.

FIGS. 4E and 4F depict another embodiment of electrode assembly 220, in which the first electrode array comprises a single wire electrode 232, and the second electrode array comprises a single pair of curved "L"-shaped electrodes 242, in cross-section. Typical dimensions, where different than what has been stated for earlier-described embodiments, are X1≈12 mm, Y1≈6 mm, Y2≈3 mm, and L1≈3 mm. The effective R2/R1 ratio is again greater than about 20:1. The fewer electrodes comprising assembly 220 in FIGS. 4E and 4F promote economy of construction, and ease of cleaning, although more than one electrode 232, and more than two electrodes 242 could of course be employed. This embodiment again incorporates the staggered symmetry described earlier, in which electrode 232 is equidistant from two electrodes 242.

Figure 4G:
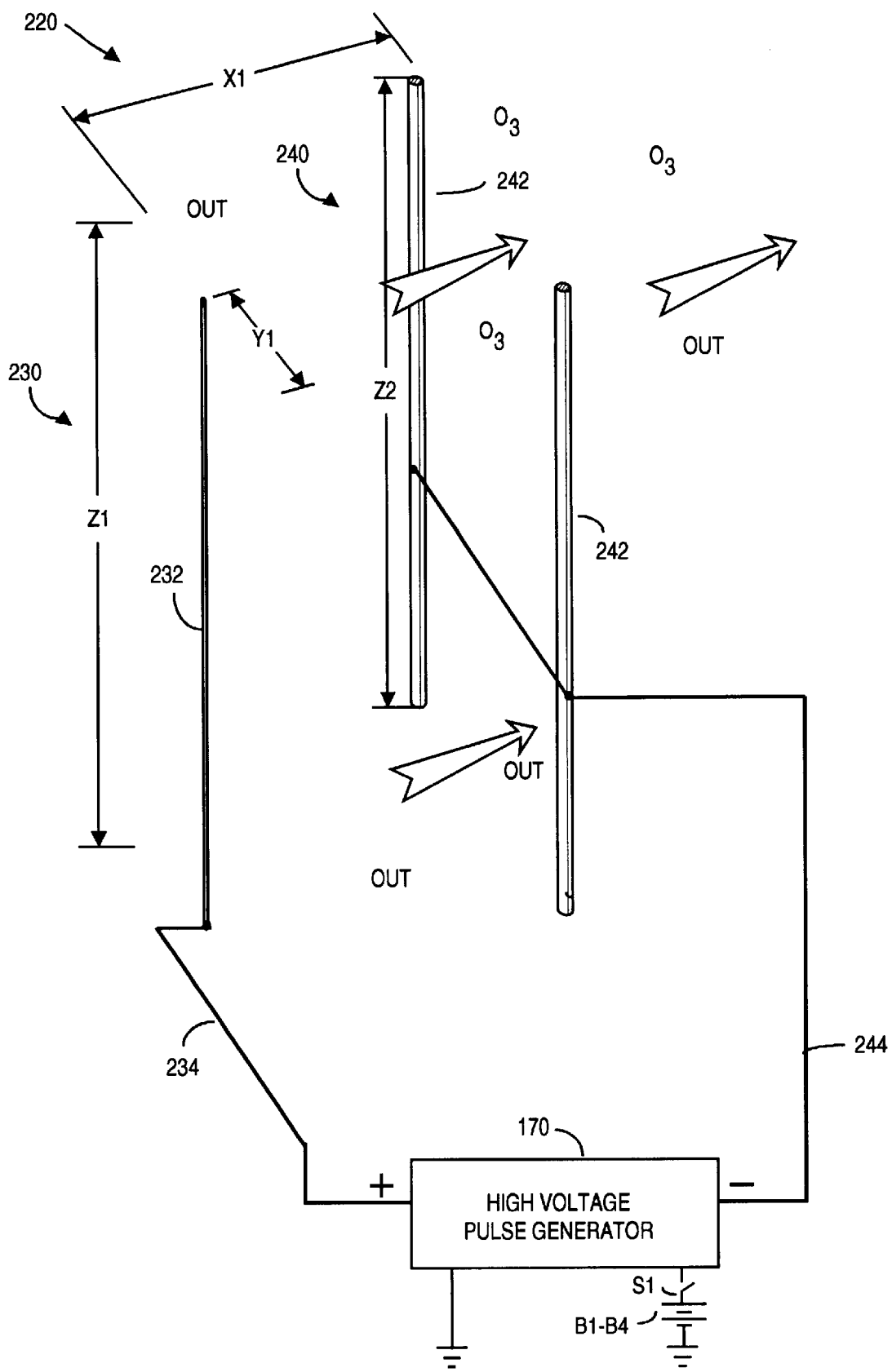
FIG. 4G is a perspective block diagram showing a fourth embodiment for an electrode assembly, according to the present invention.
Figure 4H:
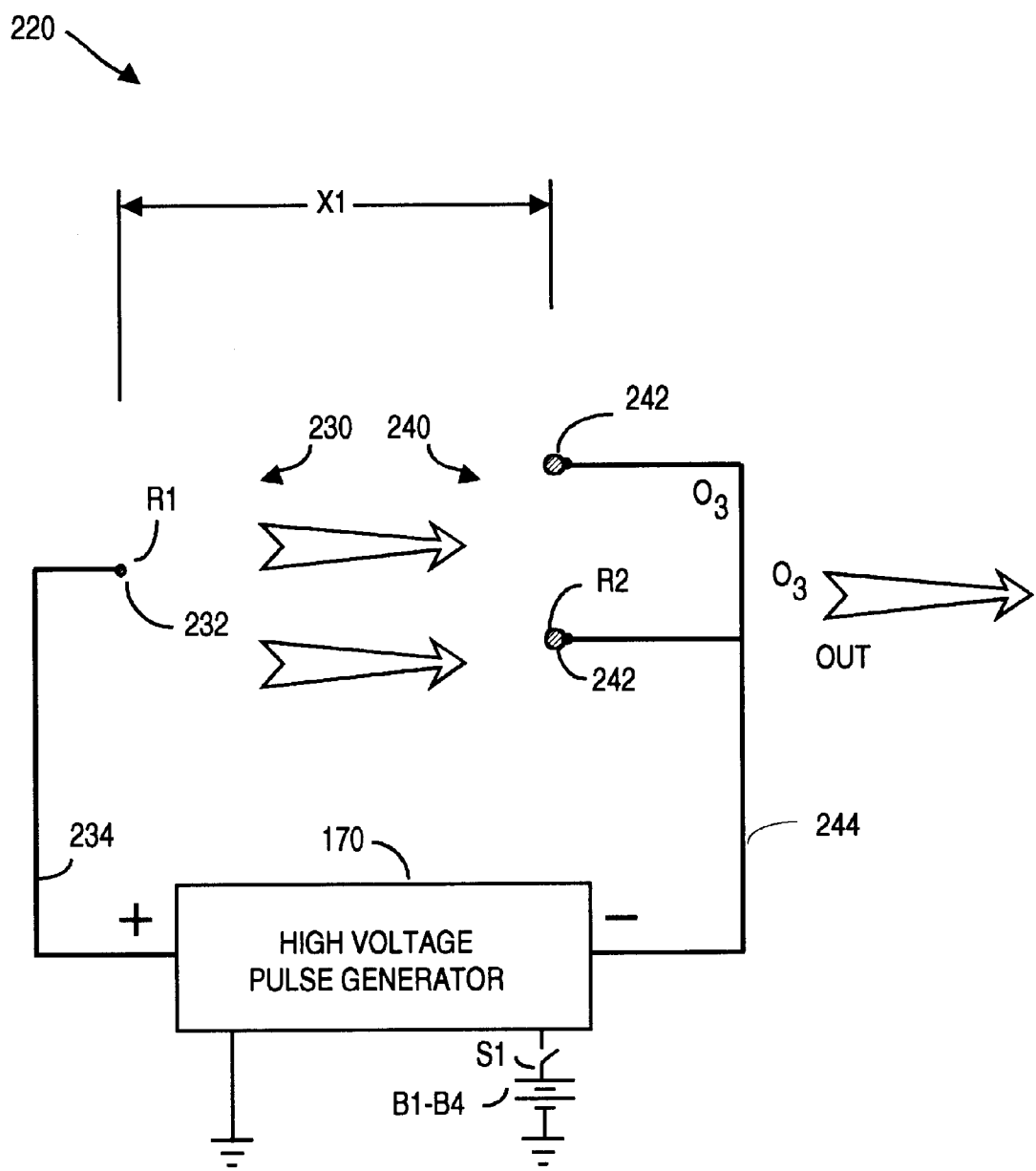
FIG. 4H is a plan block diagram of the embodiment of FIG. 4G.

FIGS. 4G and 4H shown yet another embodiment for electrode assembly 220. In this embodiment, first electrode array 230 is a length of wire 232, while the second electrode array 240 comprises a pair of rod or columnar electrodes 242. As in embodiments described earlier herein, it is preferred that electrode 232 be symmetrically equidistant from electrodes 242. Wire electrode 232 is preferably perhaps 0.08 mm tungsten, whereas columnar electrodes 242 are perhaps 2 mm diameter stainless steel. Thus, in this embodiment the R2/R1 ratio is about 25:1. Other dimensions may be similar to other configurations, e.g., FIG. 4E, 4F. Of course electrode assembly 220 may comprise more than one electrode 232, and more than two electrodes 242.

Figure 4I:
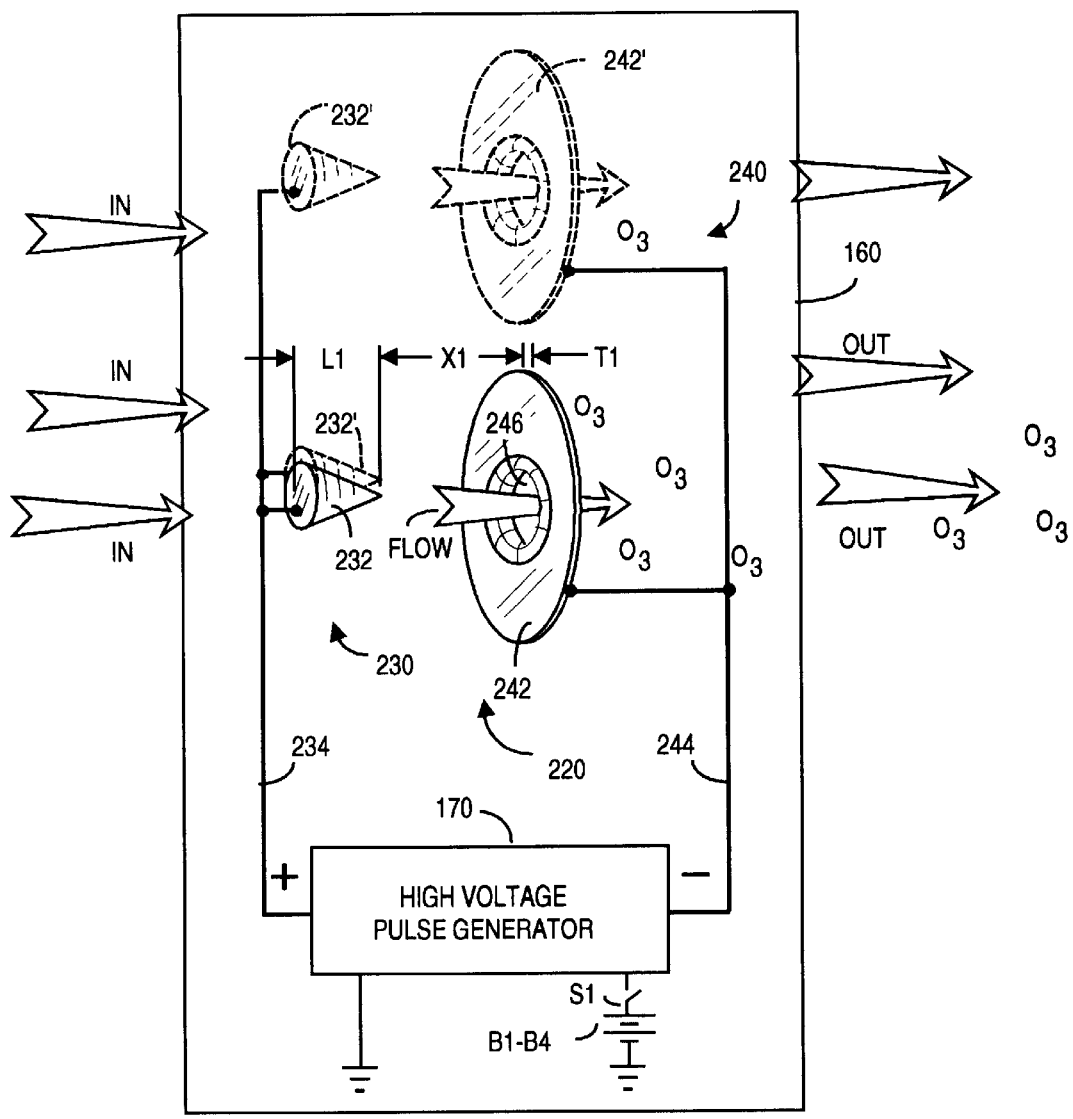
FIG. 4I is a perspective block diagram showing a fifth embodiment for an electrode assembly, according to the present invention.
Figure 4J:
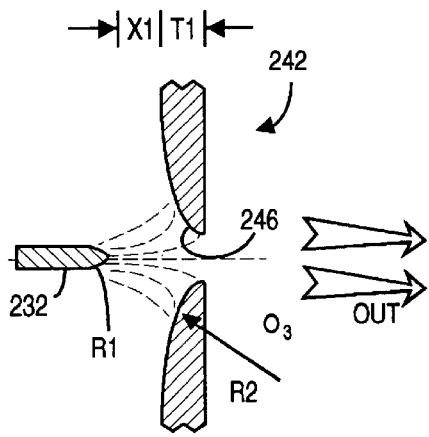
FIG. 4J is a detailed cross-sectional view of a portion of the embodiment of FIG. 4I.

An especially preferred embodiment is shown in FIG. 4I and FIG. 4J. In these figures, the first electrode assembly comprises a single pin-like element 232 disposed coaxially with a second electrode array that comprises a single ring-like electrode 242 having a rounded inner opening 246. However, as indicated by phantom elements 232', 242', electrode assembly 220 may comprise a plurality of such pin-like and ring-like elements. Preferably electrode 232 is tungsten, and electrode 242 is stainless steel.

Typical dimensions for the embodiment of FIG. 4I and FIG. 4J are L1≈10 mm, X1≈9.5 mm, T≈0.5 mm, and the diameter of opening 246 is about 12 mm. Dimension L1 preferably is sufficiently long that upstream portions of electrode 232 (e.g., portions to the left in FIG. 4I) do not interfere with the electrical field between electrode 232 and the collector electrode 242. However, as shown in FIG. 4J, the effect R2/R1 ratio is governed by the tip geometry of electrode 232. Again, in the preferred embodiment, this ratio exceeds about 20:1. Lines drawn in phantom in FIG. 4J depict theoretical electric force field lines, emanating from emitter electrode 232, and terminating on the curved surface of collector electrode 246. Preferably the bulk of the field emanates within about +45° of coaxial axis between electrode 232 and electrode 242. On the other hand, if the opening in electrode 242 and/or electrode 232 and 242 geometry is such that too narrow an angle about the coaxial axis exists, air flow will be unduly restricted. One advantage of the ring-pin electrode assembly configuration shown in FIG. 4I is that the flat regions of ring-like electrode 242 provide sufficient surface area to which dust entrained in the moving air stream can attach, yet be readily cleaned. As a result, the air stream (OUT) emitted by device 100 has reduced dust content, especially contrasted to prior art kinetic air mover configurations. Thus, in addition to being sanitized and deodorized, dust or dirt particles within the footwear may be removed.

Further, the ring-pin configuration advantageously generates more ozone than prior art configurations, or the configurations of FIGS. 4A–4H. For example, whereas the configurations of FIGS. 4A–4H may generate perhaps 50 ppb ozone, the configuration of FIG. 4I can generate about 2,000 ppb ozone, without an increase in demand upon power supply B1.

Figure 4K:
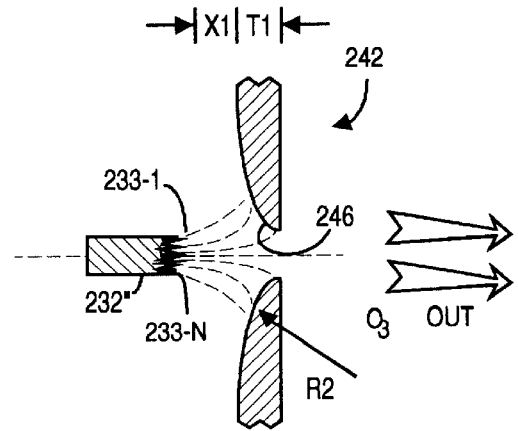
FIG. 4K is a detailed cross-sectional view of a portion of an alternative to the embodiment of FIG. 4I.

Nonetheless it will be appreciated that applicants' first array pin electrodes may be utilized with the second array electrodes of FIGS. 4A–4H. Further, applicants' second array ring electrodes may be utilized with the first array electrodes of FIGS. 4A–4H. For example, in modifications of the embodiments of FIGS. 4A–4H, each wire or columnar electrode 232 is replaced by a column of electrically series-connected pin electrodes (e.g., as shown in FIGS. 4I–4K), while retaining the second electrode arrays as depicted in these figures. By the same token, in other modifications of the embodiments of FIGS. 4A–4H, the first array electrodes can remain as depicted, but each of the second array electrodes 242 is replaced by a column of electrically series-connected ring electrodes (e.g., as shown in FIGS. 4I–4K).

In FIG. 4J, a detailed cross-sectional view of the central portion of electrode 242 in FIG. 4I is shown. As best seen in FIG. 4J, curved region 246 adjacent the central opening in electrode 242 appears to provide an acceptably large surface area to which many ionization paths from the distal tip of electrode 232 have substantially equal path length. Thus, while the distal tip (or emitting tip) of electrode 232 is advantageously small to concentrate the electric field between the electrode arrays, the adjacent regions of electrode 242 preferably provide many equidistant inter-electrode array paths. A high exit flowrate of perhaps 90 feet/minute and 2,000 ppb range ozone emission attainable with this configuration confirm a high operating efficiency.

In FIG. 4K, one or more electrodes 232 is replaced by a conductive block 232" of carbon fibers, the block having a distal surface in which projecting fibers 233-1, . . . 233-N take on the appearance of a "bed of nails". The projecting fibers can each act as-an emitting electrode and provide a plurality of emitting surfaces. Over a period of time, some or all of the electrodes will literally be consumed, whereupon graphite block 232" will be replaced. Materials other than graphite may be used for block 232" providing the material has a surface with projecting conductive fibers such as 233-N.

Figure 5:
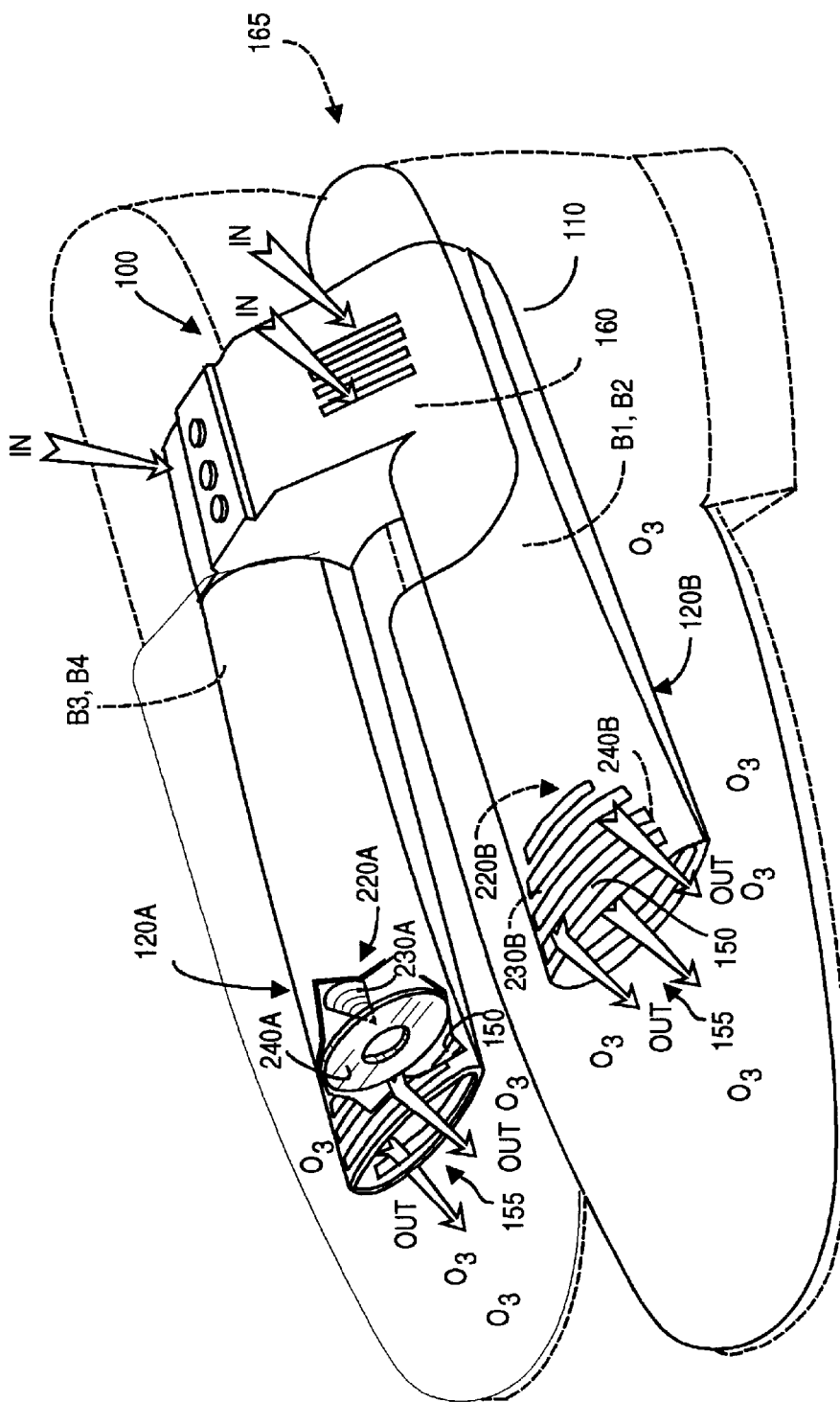
FIG. 5 is a partial cutaway perspective view of the present invention showing location of the electrode assemblies, according to the present invention.

FIG. 5 shows member 120A partially cutaway to depict the location of a typical electrode assembly 220A. In FIG. 5, electrode assembly 220A includes first and second arrays 230A and 240A, whose electrodes are similar to that depicted in FIG. 4I. Although FIG. 5 depicts electrode assemblies 220 with the ring-pin configuration of FIG. 4I, it is understood that any of the alternative configurations of FIGS. 4A–4G could instead be contained within members 120A, 120B. Indeed, there is no requirement that the present invention provide two projecting members 120A and 120B. If desired, the present invention could be implemented with a single projecting member, e.g., member 120A, although providing more than one member reduces the time necessary to sanitize a pair of footwear. By the same token, the present invention could be implemented with more than two pairs of projecting members, e.g., perhaps four pairs, to permit sanitizing more than one pair of footwear simultaneously.

Preferably the inner distal portions of members 120 include an electrostatic shield that reduces detectable electromagnetic radiation external to device 100. For example, a metal shield could be disposed within members 120, or portions of the interior of members 120 could be coated with a metallic paint to reduce such radiation.

It will also be appreciated that the net output of ions could be influenced by placing a bias element near some or all of the output vents. For example, such an element could be electrically biased to neutralize negative ions, thereby increasing the net output of positive ions. It will also be appreciated that the present invention could be adjusted to produce ions without producing ozone, if desired.

Modifications and variations may be made to the disclosed embodiments without departing from the subject and spirit of the invention as defined by the following claims.

What is claimed is:

1. A self-contained ion and ozone emitting device for sanitizing footwear, comprising:
    a device housing defining at least one inlet vent and including a first projecting member defining a first outlet vent, sized to fit within a first piece of footwear, and a second projecting member defining a second outlet vent, sized to fit within a second piece of footwear and spaced-apart from said first projecting member a distance permitting said first projecting member to fit within the first piece of footwear while said second projecting members fits within the second piece of footwear;
    a high voltage generator, disposed within said housing;
    a first electrode assembly within said first projecting member;
    a second electrode assembly within said second projecting member;
    wherein when operating potential is provided to said generator, said first electrode assembly produces a first air flow including ions and ozone that exits said first outlet vent and flows toward footwear surrounding said first projecting member, and said second electrode assembly produces a second air flow that includes ions and ozone that exits said second outlet vent and flows toward footwear surrounding said second projecting member.

2. A method of sanitizing footwear with a flow of ionized air containing ozone, the method comprising:
    providing a housing including at least a first projecting member, a first electrode array and a second electrode array; and
    inserting said projecting member at least partially into a piece of said footwear;
    said first electrode array includes at least one metal wire electrode;
    said second electrode array includes at least two electrically conductive rod electrodes, said rod electrodes being equidistant from said metal wire electrode; and
    wherein an interior region of said footwear is subject to a flow of ionized air including ozone.

3. A self-contained ion and ozone emitting device for sanitizing footwear, comprising:
    a device housing defining at least one vent and including a first projecting member, sized to fit within a first piece of footwear;
    a high voltage generator, disposed within said housing; and
    a first electrode assembly disposed within said first projecting member, comprising:
        at least one electrically conductive pin-shaped electrode electrically coupled to a first output port of said generator; and
        at least one electrically conductive ring-shaped electrode defining an opening and being electrically coupled to a second output port of said generator, said ring-shaped electrode including a flat surface area region generally facing said pin-shaped electrode;
    wherein when operating potential is provided to said generator, said first electrode assembly produces ionized air that flows from said pin-shaped electrode toward said ring-shaped electrode, such that air exiting said vent includes ions and ozone and flows toward footwear surrounding said first projecting member,
    wherein said housing further includes a second projecting member with a second vent, sized to fit within a second piece of footwear and spaced-apart from said first projecting member a distance permitting said first projecting member to fit within the first piece of footwear while said second projecting members fits within the second piece of footwear,
    a second electrode assembly disposed within said second projecting member, said second electrode assembly comprising:
        at least a second electrically conductive pin-shaped electrode electrically coupled to said first output port of said generator; and
        at least a second electrically conductive ring-shaped electrode defining an opening and being electrically coupled to said second output port of said generator; and
        wherein when operating potential is provided to said generator, said second electrode assembly produces ionized air that flows from said second pin-shaped electrode toward said second ring-shaped electrode, such that air exiting said second vent includes ions and ozone and flows toward footwear surrounding said second projecting member.

4. A method of sanitizing footwear with a flow of ionized air containing ozone, the method comprising:
    selecting a device including at least a first projecting member, where said device includes an electrode assembly comprising a first electrode, a second electrode, and a high voltage generator, having a first output port electrically coupled to said first electrode, and further having a second output port electrically coupled to said second electrode, where said first electrode includes at least one metal wire electrode, said second electrode includes at least two electrically conductive rod-shaped electrodes, said rod-like electrodes being equidistant from said metal wire electrode; and inserting said projecting member at least partially into a piece of said footwear; and subjecting an interior region of said footwear to a flow of ionized air including ozone.

5. An ion emitting device adapted to sanitize footwear, comprising:
   a housing including at least a first projecting member, adapted for insertion into a first piece of footwear, and a second projecting member, adapted for insertion into a second piece of footwear and spaced-apaft from said first projecting member a distance permitting said first projecting member to fit within the first piece of footwear while said second projecting member fits within the second piece of footwear;
   an electrode assembly within each of said first and second projecting members, each electrode assembly comprising a first electrode and a second electrode, where said first electrode includes at least one metal wire electrode, and further where said second electrode includes at least two electrically conductive rod electrodes with said rod electrodes being spaced from said metal wire electrode; and
   a high voltage generator having a first output port operably coupled to the first electrode and a second output port operably coupled to the second electrode.

6. The device of claim 5, wherein said housing includes at least one inlet vent and first and second outlet vents, where said first outlet vent is located in said first projecting member so as to be disposable in the first piece of footwear when said first projecting member is disposed in the first piece of footwear, where said second outlet vent is located in said second projecting member so as to be disposable in the second piece of footwear when said second projecting member is disposed in the second piece of footwear, and further where said at least one inlet vent is located distally from said first and second outlet vents so as to communicate with ambient air and extend out of the footwear when the first projecting member and the second projecting member are each disposed in footwear.

7. An ion emitting device adapted to sanitize footwear, comprising:
   a housing including at least a first projecting member which is adapted for insertion into footwear;
   an electrode assembly comprising a first electrode and a second electrode, where said first electrode includes at least one metal wire electrode, and further where said second electrode includes at least two electrically conductive rod electrodes; and
   a high voltage generator having a first output port operably coupled to the first electrode and a second output port operably coupled to the second electrode;
   wherein said housing includes an inlet vent and an outlet vent, where said outlet vent is located in said first projecting member so as to be disposable in footwear when said first projecting member is disposed in footwear, and further where said inlet vent is located distally from said outlet vent so as to communicate with ambient air and extend out of the footwear when the first projecting member is disposed in footwear.

8. An ion emitting device adapted to sanitize footwear, comprising:
   a housing including at least a first projecting member which is adapted for insertion into footwear;
   an electrode assembly comprising a first electrode and a second electrode, where said first electrode includes at least one metal wire electrode, and further where said second electrode includes at least two electrically conductive U-shaped electrodes; and
   a high voltage generator having a first output port operably coupled to the first electrode and a second output port operably coupled to the second electrode.

9. The device of claim 8, wherein said housing includes an inlet vent and an outlet vent, where said outlet vent is located in said first projecting member so as to be disposable in footwear when said first projecting member is disposed in footwear; and further where said inlet vent is located distally from said outlet vent so as to communicate with ambient air and extend out of the footwear when the first projecting member is disposed in footwear.

10. An ion emitting device adapted to sanitize footwear, comprising:
    a housing including at least a first projecting member which is adapted for insertion into footwear;
    an electrode assembly comprising a first electrode and a second electrode, where said first electrode includes at least one metal wire electrode, and further where said second electrode includes at least two electrically conductive U-shaped electrodes with pointed regions; and
    a high voltage generator having a first output port operably coupled to the first electrode and a second output port operably coupled to the second electrode.

11. The device of claim 10, wherein said housing includes an inlet vent and an outlet vent, where said outlet vent is located in said first projecting member so as to be disposable in footwear when said first projecting member is disposed in footwear, and further where said inlet vent is located distally from said outlet vent so as to communicate with ambient air and extend out of the footwear when the first projecting member is disposed in footwear.

12. An ion emitting device adapted to sanitize footwear, comprising:
    a housing including at least a first projecting member which is adapted for insertion into footwear;
    an electrode assembly comprising a first electrode and a second electrode, where said first electrode includes at least one metal wire electrode, and further where said second electrode including at least two electrically conductive L-shaped electrodes; and
    a high voltage generator having a first output port operably coupled to the first electrode and a second output port operably coupled to the second electrode.

13. The device of claim 12, wherein said housing includes an inlet vent and an outlet vent, where said outlet vent is located in said first projecting member so as to be disposable in footwear when said first projecting member is disposed in footwear, and further where said inlet vent is located distally from said outlet vent so as to communicate with ambient air and extend out of the footwear when the first projecting member is disposed in footwear.

14. A self-contained ion and ozone emitting device for sanitizing footwear, comprising:
    a device housing including:
        a first projecting member sized to fit within a first piece of footwear;
        a second projecting member sized to fit within a second piece of footwear;
        a bridge spacing said first projecting member from the second projecting member a sufficient distance to permit said first projecting member to fit within the first piece of footwear while said second projecting member fits within the second piece of footwear;
        a first outlet vent located in said first projecting member; and a second outlet vent located in said second projecting member;

at least one inlet vent located in said bridge to communicate with ambient air and extend out of the first and second pieces of footwear when said first projecting member is disposed in the first piece of footwear and said second projecting member is disposed in the second piece of footwear;

an ion and ozone generator disposed in said housing, that draws ambient air in through said at least one inlet vent and creates electrostatic flows of air that travel in a downstream direction from said at least one inlet vent to said first and second outlet vents, said ion and ozone generator including:

a high voltage generator, disposed within said housing;

a first electrode assembly disposed in said first projecting member and electrically coupled with said high voltage generator, said first electrode assembly producing both ions and ozone that exit said first outlet vent and flow towards the first piece of footwear when said first projecting member is disposed in the first piece of footwear; and a second electrode assembly located in said second projecting member and electrically coupled with said high voltage generator, said second electrode assembly producing both ions and ozone that exit said second outlet vent and flow toward the second piece of footwear when said second projecting member is disposed in the second piece of footwear.

15. The device of claim 14, wherein at least one of the first and second electrode assemblies comprises a first electrode array and a second electrode array, said first electrode array including at least one electrode that has a base and an apex, said base being wider than said apex, and said apex aimed generally in the downstream direction and generally toward said second electrode array, said second electrode array including at least one electrically conductive member through which there is defined at least one opening disposed generally in front of said apex.

16. The device of claim 14, wherein at least one of the first and second electrode assemblies comprises:

at least one electrically conductive pin-shaped electrode electrically coupled to a first output port of said generator; and at least one electrically conductive ring-shaped electrode defining an opening and being electrically coupled to a second output port of said generator, said ring-shaped electrode being disposed coaxial with and in a downstream direction from a tapered end of said pin-shaped electrode.

17. The device of claim 14, wherein at least one of the first and second electrode assemblies comprises a first electrode and a second electrode, where said first electrode includes at least one metal wire electrode, and further where said second electrode includes at least two electrically conductive U-shaped electrodes.

18. A self-contained ion and ozone emitting device for sanitizing footwear, comprising: a device housing including:

a first projecting member sized to fit within a first piece of footwear;

a second projecting member spaced sized to fit within a second piece of footwear;

a bridge spacing said first projecting member from the second projecting member a sufficient distance to permit said first projecting member to fit within the first piece of footwear while said second projecting member fits within the second piece of footwear, said bridge including a center console and first and second angled portions, said first angled portion projecting at an angle from said center console to said first projecting member, said second angled portion projecting at an angle from said center console to said second projecting member;

a first outlet vent located in said first projecting member; and a second outlet vent located in said second projecting member;

at least one inlet vent located in said first and second portions of said bridge to communicate with ambient air and extend out of the first and second pieces of footwear when said first projecting member is disposed in the first piece of footwear and said second projecting member is disposed in the second piece of footwear;

an ion and ozone generator disposed in said housing, that draws ambient air in through said at least one inlet vent and creates electrostatic flows of air that travel in a downstream direction from said at least one inlet vent to said first and second outlet vents, said ion and ozone generator including:

a high voltage generator, disposed within said housing;

a first electrode assembly disposed in said first projecting member and electrically coupled with said high voltage generator, said first electrode assembly producing both ions and ozone that exit said first outlet vent and flow towards the first piece of footwear when said first projecting member is disposed in the first piece of footwear; and a second electrode assembly located in said second projecting member and electrically coupled with said high voltage generator, said second electrode assembly producing both ions and ozone that exit said second outlet vent and flow toward the second piece of footwear when said second projecting member is disposed in the second piece of footwear.

19. A self-contained ion and ozone emitting device for sanitizing footwear, comprising:

a device housing including:

a first projecting member sized to fit within a first piece of footwear;

a second projecting member spaced sized to fit within a second piece of footwear;

a bridge spacing said first projecting member from the second projecting member a sufficient distance to permit said first projecting member to fit within the first piece of footwear while said second projecting member fits within the second piece of footwear;

a first outlet vent located in said first projecting member;

a second outlet vent located in said second projecting member;

at least one user control located on said bridge that is accessible when said first projecting member is disposed in the first piece of footwear and said second projecting member is disposed in the second piece of footwear; and an ion and ozone generator disposed in said housing, that draws ambient air in through said at least one inlet vent and creates electrostatic flows of air that travel in a downstream direction from said at least one inlet vent to said first and second outlet vents, said ion and ozone generator including:

a high voltage generator, disposed within said housing;

a first electrode assembly disposed in said first projecting member and electrically coupled with said high voltage generator, said first electrode assembly producing both ions and ozone that exit said first outlet vent and flow towards the first piece of footwear when said first projecting member is disposed in the first piece of footwear; and a second electrode assembly located in said second projecting member and electrically coupled with said high voltage generator, said second electrode assembly producing both ions and ozone that exit said second outlet vent and flow toward the second piece of footwear when said second projecting member is disposed in the second piece of footwear.

20. A method of sanitizing footwear with a flow of ionized air containing ozone, the method comprising:

providing a housing including at least a first projecting member, a first electrode array and a second electrode array; and inserting said projecting member at least partially into a piece of said footwear;

said first electrode array includes at least one metal wire electrode;

said second electrode array includes at least two electrically conductive rod electrodes, said rod electrodes being spaced from said metal wire electrode; and wherein an interior region of said footwear is subject to a flow of ionized air including ozone.

21. A method of sanitizing footwear with a flow of ionized air containing ozone, the method comprising:

providing a housing including at least a first projecting member, a first electrode array and a second electrode array; and inserting said projecting member at least partially into a piece of said footwear;

said first electrode array includes at least one electrode that has a base and an apex, said base being wider than said apex, and said apex aimed generally in the downstream direction and generally toward said second electrode array;

said second electrode array includes at least one electrically conductive member through which there is defined at least one opening disposed generally in front of said apex;

wherein an interior region of said footwear is subject to a flow of ionized air including ozone.

22. A method of sanitizing footwear with a flow of ionized air containing ozone, the method comprising:

selecting a device including at least a first projecting member, where said device includes an electrode assembly comprising a first electrode array, a second electrode array, and a high voltage generator, having a first output port electrically coupled to said first electrode array, and further having a second output port electrically coupled to said second electrode array, where said first electrode array includes at least one metal wire electrode, said second electrode array includes at least two electrically conductive rod-shaped electrodes, said rod-like electrodes being spaced from said metal wire electrode; and inserting said projecting member at least partially into a piece of said footwear; and subjecting an interior region of said footwear to a flow of ionized air including ozone.

23. A method of sanitizing footwear with a flow of ionized air containing ozone, the method comprising:

selecting a device including at least a first projecting member, where said device includes an electrode assembly comprising a first electrode array, a second electrode array, and a high voltage generator, having a first output port electrically coupled to said first electrode, and further having a second output port electrically coupled to said second electrode array, where said first electrode array includes at least one pin shaped electrode aimed generally toward said second electrode array, and said second electrode array includes at least one electrically conductive member through which there is defined at least one opening disposed generally in front of a free end of said pin shaped electrode; and inserting said projecting member at least partially into a piece of said footwear; and subjecting an interior region of said footwear to a flow of ionized air including ozone.

24. A self-contained ion and ozone emitting device for sanitizing footwear, comprising:

a device housing including an inlet vent, a projecting member sized to fit within footwear, and an outlet vent located in said projecting member, said inlet vent being located at or a near an opposite end of said housing from said outlet vent so as to communicate with ambient air and extend out of the footwear when said first projecting member is disposed in footwear;

a high voltage generator, disposed within said housing;

an electrode assembly disposed within said first projecting member and comprising:

at least one electrically conductive pin-shaped electrode electrically coupled to a first output port of said generator, said pin-shaped electrode being located closer to the inlet vent than to the outlet vent; and at least one electrically conductive electrode, defining an opening, being electrically coupled to a second output port of said generator, and being located closer to the inlet vent than to the outlet vent;

wherein said projecting member includes an upper half within which the inlet vent is located and a lower half within which the outlet vent is located, said electrode assembly being located in said lower half; and wherein when operating potential is provided to said generator, said electrode assembly produces ionized air that flows electrostatically from said pin-shaped electrode toward said opening, such that air exiting said outlet vent includes ions and ozone and flows toward the footwear surrounding said projecting member.

25. The device of claim 24, wherein at least a portion of the upper half of the projecting member is angled relative to the lower half so that said angled portion of the upper half extends out of the footwear when the lower half is within the footwear, said inlet vent being with said angled portion of the upper half.

* * * * *